(12) United States Patent
Schreiner et al.

(10) Patent No.: US 6,677,300 B1
(45) Date of Patent: Jan. 13, 2004

(54) TREATMENT OF MICROVASCULAR ANGIOPATHIES

(75) Inventors: George F. Schreiner, Los Altos Hills, CA (US); Richard J. Johnson, Seattle, WA (US)

(73) Assignee: Scios, Inc., Sunnyvale, CA (US)

( * ) Notice: Subject to any disclaimer, the term of this patent is extended or adjusted under 35 U.S.C. 154(b) by 0 days.

(21) Appl. No.: 09/392,931

(22) Filed: Sep. 9, 1999

Related U.S. Application Data

(60) Provisional application No. 60/126,615, filed on Mar. 27, 1999, provisional application No. 60/126,406, filed on Mar. 26, 1999, and provisional application No. 60/099,694, filed on Sep. 9, 1998.

(51) Int. Cl.[7] .................... A61K 38/00; A61K 29/00; C07K 14/00; C12N 15/63
(52) U.S. Cl. .................... 514/2; 424/198.1; 530/350; 435/455
(58) Field of Search .................... 514/2; 435/455; 424/198.1; 530/350

(56) References Cited

U.S. PATENT DOCUMENTS

| | | | |
|---|---|---|---|
| 5,332,671 A | * | 7/1994 | Ferrara et al. ........... 435/240.1 |
| 5,714,458 A | * | 2/1998 | Adami et al. ................ 514/2 |
| 5,941,868 A | * | 8/1999 | Kaplan et al. ............. 604/500 |
| 5,980,887 A | * | 11/1999 | Isner et al. ............... 424/93.7 |

OTHER PUBLICATIONS

Asahara et al., "Accelerated restitution of Endothelial Integrity and Endothelium–Dependent Function After phVEGF165 Gene Transfer" *Circulation* 94(12):3291–3301 (1996).

Takahashi et al., " Renal microvascular assembly and repair: Power and promise of molecular definition" *Kidney International* 53:826–835 (1998).

* cited by examiner

*Primary Examiner*—Gary Kunz
*Assistant Examiner*—Janet L. Andres
(74) *Attorney, Agent, or Firm*—Morrison & Foerster LLP

(57) ABSTRACT

The invention concerns the prevention and treatment of endothelial injury and the injury of tissues containing injured blood vessels by administration of angiogenic factors, such as vascular endothelial cell growth factor (VEGF).

28 Claims, 9 Drawing Sheets hVEGF121

ATGAACTTTCTGCTGTCTTGGGTGCATTGGAGCCTTGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAATGTGACAAGCCGAGGCGGTGA

FIG. 2 hVEGF121

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKCDKPRR

FIG. 3 hVEGF145

ATGAACTTTCTGCTGTCTTGGGTGGATTGGAGCCTTGCCTTGCTGCTCTACCTCCACCATGCCAAGTG
GTCCCAGGCTGCACCCATGGCAGAAGGAGGAGGGCAGAATCATCACGAAGTGGTGAAGTTCATGGAT
GTCTATCAGCGCAGCTACTGCCATCCAATCGAGACCCTGGTGGACATCTTCCAGGAGTACCCTGATGA
GATCGAGTACATCTTCAAGCCATCCTGTGTGCCCCTGATGCGATGCGGGGGCTGCTGCAATGACGAG
GGCCTGGAGTGTGTGCCCACTGAGGAGTCCAACATCACCATGCAGATTATGCGGATCAAACCTCACCA
AGGCCAGCACATAGGAGAGATGAGCTTCCTACAGCACAACAAATGTGAATGCAGACCAAAGAAAGATA
GAGCAAGACAAGAAAAAAAATCAGTTCGAGGAAAGGGAAAGGGGCAAAAACGAAAGCGCAAGAAATC
CCGGTATAAGTCCTGGAGCGTATGTGACAAGCCGAGGCGGTGA

FIG. 4 hVEGF145

APMAEGGGQNHHEVVKFMDVYQRSYCHPIETLVDIFQEYPDEIEYIFKPSCVPLMRCGGCCNDEG
LECVPTEESNITMQIMRIKPHQGQHIGEMSFLQHNKCECRPKKDRARQEKKSVRGKGKGQKRKRK
KSRYKSWSVCDKPRR

FIG. 5 hVEGF 165

ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTCCTC
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAATCCCTGTGGGCCTTGCTCAGAGCGGAGAAAGCA
TTTGTTTGTACAAGATCCGCAGACGTGTAAATGTTCCTGCAAAAACACAGACTCGCGTTGCAAGG
CGAGGCAGCTTGAGTTAAACGAACGTACTTGCAGATGTGACAAGCCGAGGCGGTGA

FIG. 6 hVEGF165

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQENPCGPCSERRKHLFVQDPQTCKCSCKNTDSRCKARQLELNERTCRCDKPRR

FIG. 7 hVEGF189

ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAAAATCAGTTCGAGGAAAGGGAAAGGGGCAAAA
ACGAAAGCGCAAGAAATCCCGGTATAAGTCCTGGAGCGTGGGCCTTGCTCAGAGCGGAGAAAGC
ATTTGTTTGTACAAGATCCGCAGACGTGTAAATGTTCCTGCAAAAACACAGACTCGCGTTGCAAG
GCGAGGCAGCTTGAGTTAAACGAACGTACTTGCAGATGTGACAAGCCGAGGCGGTGA

FIG. 8 hVEGF189

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVPCGPCSERRKHLFVQDPQTCKCSCKNTDSR
CKARQLELNERTCRCDKPRR

FIG. 9 hVEGF 206

ATGAACTTTCTGCTGTCTTGGGTGCATTGGAGCCTCGCCTTGCTGCTCTACCTCCACCATGCCAA
GTGGTCCCAGGCTGCACCCATGGCAGAAGGAGGAGGGCAGAATCATCACGAAGTGGTGAAGTTCA
TGGATGTCTATCAGCGCAGCTACTGCCATCCAATCGAGACCCTGGTGGACATCTTCCAGGAGTAC
CCTGATGAGATCGAGTACATCTTCAAGCCATCCTGTGTGCCCCTGATGCGATGCGGGGGCTGCTG
CAATGACGAGGGCCTGGAGTGTGTGCCCACTGAGGAGTCCAACATCACCATGCAGATTATGCGGA
TCAAACCTCACCAAGGCCAGCACATAGGAGAGATGAGCTTCCTACAGCACAACAAATGTGAATGC
AGACCAAAGAAAGATAGAGCAAGACAAGAAAAAAAATCAGTTCGAGGAAAGGGAAAGGGGCAAAA
ACGAAAGCGCAAGAAATCCCGGTATAAGTCCTGGAGCGTGTACGTTGGTGCCCGCTGCTGTCTAA
TGCCCTGGAGCCTCCCTGGCCCCCATCCCTGTGGGCCTTGCTCAGAGCGGAGAAAGCATTTGTTT
GTACAAGATCCGCAGACGTGTAAATGTTCCTGCAAAAACACAGACTCGCGTTGCAAGGCGAGGCA
GCTTGAGTTAAACGAACGTACTTGCAGATGTGACAAGCCGAGGCGGTGA

FIG. 10 hVEGF206

MNFLLSWVHWSLALLLYLHHAKWSQAAPMAEGGGQNHHEVVKFMDVYQRSYCHPIETLVDIFQEY
PDEIEYIFKPSCVPLMRCGGCCNDEGLECVPTEESNITMQIMRIKPHQGQHIGEMSFLQHNKCEC
RPKKDRARQEKKSVRGKGKGQKRKRKKSRYKSWSVYVGARCCLMPWSLPGPHPCGPCSERRKHLF
VQDPQTCKCSCKNTDSRCKARQLELNERTCRCDKPRR.

FIG. 11 hVEGF110

APMAEGGGQNHHEVVKFMDVYQRSYCHPIETLVDIFQEYPDEIEYIFKPSCVPLMRCGGCCNDEG
LECVPTEESNITMQIMRIKPHQGQHIGEMSFLQHNKCECRPKKDR

FIG. 12

TREATMENT OF MICROVASCULAR ANGIOPATHIES

CROSS-REFERENCE TO RELATED APPLICATIONS

This is a non-provisional application of co-pending provisional application Serial No. 60/099,694 filed on Sep. 9, 1998, of provisional application Serial No. 60/126,406 filed Mar. 26, 1999 and of provisional application Serial No. 60/126,615 filed Mar. 27, 1999, the disclosures of which are hereby incorporated by reference and to which application priority is claimed under 35 USC 119.

FIELD OF THE INVENTION

The present invention concerns the treatment of endothelial cell injury. More particularly, the invention concerns the treatment of the endothelium of blood vessels and tissues containing injured blood vessels. The invention specifically concerns the prevention or repair of injury to blood vessels, and, in particular, the treatment of disorders characterized by microvascular angiopathies, such as thrombotic microangiopathies (TMA). The invention also relates to the treatment of kidney diseases associated with injury to, or atrophy of, the vasculature of the glomerulus and interstitium, and the treatment of hypoxia or hypercapnia or fibrosis arising from injury to the endothelium of the lungs.

BACKGROUND OF THE INVENTION

Acute injuries to smaller blood vessels and subsequent dysfunction of the tissue in which the injured blood vessels are located (microvascular angiopathies) are a common feature of the pathology of a variety of diseases of various organs, such as kidney, heart, and lungs. The injury is often associated with endothelial cell injury or death and the presence of products of coagulation or thrombosis. The agent of injury may, for example, be a toxin, an immune factor, an infectious agent, a metabolic or physiological stress, or a component of the humoral or cellular immune system, or may be as of yet unidentified. A subgroup of such diseases is unified by the presence of thrombotic microangiopathies (TMA), and is characterized clinically by non-immune hemolytic anemia, thrombocytopenia, and/or renal failure. The most common cause of TMA is the hemolytic uremic syndrome (HUS), a disease that more frequently occurs in childhood, where it is the most common cause of acute renal failure, but also affects adults where more severe clinical course is often observed. Although the pathogenesis of HUS has not been fully elucidated, it is widely accepted that the majority of these cases are associated with enteric infection with the verotoxin producing strain, *E. coli* O157. Verotoxins produced by *E. coli* induce glomerular. endothelial cell (GEN) injury and generate renal thrombotic microangiopathy in most cases of epidemic HUS (Boyce et. al., *N. Engl. J. Med.* 333:364–368 (1995)). Some patients, especially adults, may have a relative lack of renal involvement and are sometimes classified as having thrombotic thrombocytopenic purpura (TTP). However, thrombotic microangiopathies may also occur as a complication of pregnancy (eclampsia), with malignant hypertension following radiation to the kidney, after transplantation (often secondary to cyclosporine or FK506 treatment), with cancer chemotherapies (especially mitomycin C), with certain infections (e.g., Shigella or HIV), in association with systemic lupus or the antiphospholipid syndrome, or may be idiopathic or familial. Experimental data suggest that endothelial cell injury is a common feature in the pathogenesis of HUS/TTP. See, e.g. Kaplan et al., *Pediatr. Nephrol.* 4:276 (1990). Endothelial cell injury triggers a cascade of subsequent events, including local intravascular coagulation, fibrin deposition, and platelet activation and aggregation. The mechanisms that mediate these events are not well understood. In the case of verotoxin-mediated HUS, injury to the endothelium leads to detachment and death, with local platelet activation and consumption, fibrin deposition and microangiopathic hemolysis.

The renal corpuscule, commonly referred to as glomerulus, is composed of a capillary network lined by a thin layer of fenestrated endothelium; a central region of mesangial cells with surrounding mesangial matrix; the visceral epithelial cells and the associated basement membrane; and the parietal layer of Bowman capsule with its basement membrane. Between the two epithelial layers, there is a narrow cavity called the urinary space. The glomerulus is responsible for the production of an ultrafiltrate of plasma. The endothelial cells form the initial barrier to the passage of blood constituents from the capillary lumen to the urinary space. Under normal conditions, the formed constituents of the blood, such as erythrocytes, leukocytes, and platelets, do not gain access to the subendothelial space. In addition, because of their negative surface charge, the endothelial cells contribute to the charge-specific properties of the glomerular capillary wall. In the kidney, the damage to the glomerular and peritubular capillaries and arterioles results in ischemia and acute tubular necrosis, and, if severe, may lead to patchy or regional cortical necrosis. For further details see also Brenner & Rector's: The Kidney, Fifth Ed., Barry M. Brenner ed., W. B. Saunders Co., 1996.

The current treatment of HUS in children consists primarily of supportive therapy (dialysis, transfusions and attention to fluid and electrolyte balance). However, in adults and in refractory cases in children the addition of plasma infusion and/or plasma exchange therapy is also performed. Remuzzi and Ruggenenti, *Kidney Int.* 47:2–19 (1995). Data to support plasma exchange therapy is not conclusive, but uncontrolled trials have suggested a potential benefit, especially in terms of improving the thrombocytopenia, anemia, and associated neurologic signs (which consist of confusion, paresthesias, and occasionally coma). Most patients recover from the acute episode, although mortality rates of 3–8% are occasionally reported. Brandt and Avner, Hemolytic uremic syndrome and thrombotic thrombocytopenia purpura. In: Neilson and Couser, eds., *Immunologic Renal Diseases*, Lippincott-Raven, Philadelphia, 1996, pp. 1161–1181. However, some patients do not recover their renal function fully, and between 20 and 40% of patients will develop some degree of renal impairment or hypertension within 10–15 years, with as many as half progressing to dialysis. Brandt and Avner, supra. In 1995, HUS accounted for 2.4% of patients on dialysis. Patients at risk were those with greater than 50% glomerular involvement, arteriolar disease, or cortical necrosis. Habib et al., *Adv. Nephrology* 11:99–128 (1982).

There is a great need for new therapeutic agents for the treatment of microvascular angiopathies, and in particular, thrombotic microangiopathies (TMA). There is a particular need to find a way to preserve cells and maintain normal function of organs within which the blood vessels are undergoing, or have undergone, injury. Currently, no therapy has been proposed for the treatment of microvascular angiopathies that is targeted at preventing or reducing endothelial cell injury and stimulating the repair of injured endothelial cells. Indeed, most of the agents in clinical use are either aimed at removing or infusing unknown factors (plasma exchange/plasma infusion), inhibiting platelet action (antiplatelet drugs), or blocking the immune system (steroids and vincristine).

There is further a need for new approaches to the treatment of renal diseases involving injury to the glomerular endothelium and the tissues surrounding the injured glomerular blood vessels, and in particular, the treatment of hemolytic uremic syndrome (HUS).

SUMMARY OF THE INVENTION

The present invention concerns compositions and methods for the prevention or reduction of endothelial cell injury, or the repair of endothelial cells already injured. While the repair of injured endothelial cells might be accompanied by the formation of new blood vessels (angiogenesis), angiogenesis is not considered to be the primary mechanism of the treatments according to the present invention.

In one aspect, the invention concerns a method for the prevention or repair of injury to blood vessels by administering an effective amount of an angiogenic factor or an agonist thereof, or a factor stimulating the production of an angiogenic factor. In a particular embodiment, the injury is associated with microvascular angiopathy, such as thrombotic microangiopathy (TMA). In a further embodiment, the invention concerns the treatment of microvascular angiopathy, e.g. TMA of the kidney, heart, or lungs. In a particularly preferred embodiment, the invention concerns the prevention or repair of injury to blood vessels in association with hemolytic uremic syndrome (HUS), including thrombotic thrombocytopenic purpura (TTP).

In a particular embodiment, the invention concerns a method for the prevention or repair of injury to vascular tissue in combination with other therapies directed at the etiology or vascular injury, such as antibiotics, corticosteroids or other immunosuppressants, anti-cancer agents, plasma exchange, clot dissolving agents, etc.

In another aspect, the invention concerns a method for the prevention or repair of injury to nonvascular tissue associated with injury to blood vessels serving the tissue, by administering an effective amount of an angiogenic factor or an agonist thereof, or a factor stimulating the production of an angiogenic factor. The treatment preferably maintains the normal function of the organ comprising the nonvascular tissue, such as kidney, heart, or lungs.

In a further aspect, the invention concerns a method for the treatment of hemolytic uremic syndrome (HUS) by administering to a patient at risk of developing or having diagnosed HUS an effective amount of an angiogenic factor, or an agonist thereof, or a factor stimulating the production of an angiogenic factor.

In yet another aspect, the invention concerns a composition for the prevention or repair of injury to blood vessels comprising an effective amount of an angiogenic factor or an agonist thereof, or a factor stimulating the production of an angiogenic factor, in admixture with a carrier.

In a still further aspect, the invention concerns a composition for the prevention or repair of injury to nonvascular tissue associated with injury to blood vessels serving said tissue comprising an effective amount of an angiogenic factor or an agonist thereof, or a factor stimulating the production of an angiogenic factor, in admixture with a carrier. The composition may optionally contain one or more further agents effective in therapies directed at the etiology of vascular injury, such as antibiotic, corticosteroid, or other immunosuppressants, anti-cancer agent, clot dissolving agent, etc.

The invention also concerns an article of manufacture comprising a container, a composition within the container comprising an angiogenic factor or an agonist thereof, or a factor stimulating the production of an angiogenic factor, and instructions to use the composition for the prevention or repair of injury to blood vessels.

The invention further concerns an article of manufacture comprising a container, a composition within the container comprising an angiogenic factor or an agonist thereof, or a factor stimulating the production of an angiogenic factor, and instructions to use the composition for the prevention or repair of injury to nonvascular tissue associated with injury to blood vessels serving said tissue.

In yet another aspect, the invention concerns an article of manufacture comprising a container, a composition within the container comprising an angiogenic factor or an agonist thereof, or a factor stimulating the production of an angiogenic factor, and instructions to use the composition for the treatment of hemolytic uremic syndrome (HUS).

In a different aspect, the invention concerns a method for the prevention or repair of injury to vascular endothelial cells, comprising introducing into such endothelial cells a polynucleotide encoding an angiogenic or cytoprotective factor, an agonist thereof, or a factor stimulating the production of an angiogenic or cytoprotective factor.

In a further aspect, the invention concerns a method for the prevention or repair of injury to nonvascular tissue associated with injury to blood vessels serving such tissue, comprising introducing into such nonvascular tissue a polynucleotide encoding an angiogenic factor, an agonist thereof, or a factor stimulating the production of an angiogenic factor.

In all aspects and embodiments, the angiogenic factor may, for example, be a vascular endothelial growth factor (VEGF), or a basic or acidic fibroblast growth factor (bFGF or aFGF). The VEGF preferably is hVEGF$_{121}$ or hVEGF$_{165}$, which may, for example, be in homo- or heterodimeric form, and may be partially or fully unglycosylated. The angiogenic factors, such as VEGF, preferably exert their activity primarily via effects other than inducing new blood vessel formation.

BRIEF DESCRIPTION OF THE DRAWINGS

FIG. 2 shows a nucleotide sequence encoding native human VEGF$_{121}$ (SEQ ID NO: 1).

FIG. 3 shows the amino acid sequence of native human VEGF$_{121}$ (SEQ ID NO: 2).

FIG. 4 shows a nucleotide sequence encoding native human VEGF$_{145}$ (SEQ ID NO: 3).

FIG. 5 shows the amino acid sequence of native human VEGF$_{145}$ (SEQ ID NO: 4).

FIG. 6 shows a nucleotide sequence encoding native human VEGF$_{165}$ (SEQ ID NO: 5).

FIG. 7 shows the amino acid sequence of native human VEGF$_{165}$ (SEQ ID NO: 6).

FIG. 8 shows a nucleotide sequence encoding native human VEGF$_{189}$ (SEQ ID NO: 7).

FIG. 9 shows the amino acid sequence of native human VEGF$_{189}$ (SEQ ID NO: 8).

FIG. 10 shows a nucleotide sequence of native human VEGF$_{206}$ (SEQ ID NO: 9).

FIG. 11 shows the amino acid sequence of native human VEGF$_{206}$ (SEQ ID NO: 10).

FIG. 12 shows the amino acid sequence of native human VEGF$_{110}$ (SEQ ID NO: 11).

DETAILED DESCRIPTION OF THE INVENTION

Definitions

The phrase "angiogenic factor", as used herein, refers to any molecule (including polypeptides, peptides and small molecules), capable of promoting the growth of new blood capillary vessels from existing endothelium (angiogenesis), and/or increasing vascular permeability. Angiogenic factors include, but are not limited to, vascular endothelial growth factors (VEGFs) in all forms, including native sequence VEGF molecules from any animal species, including humans, and their functional derivatives, fibroblast growth factors (FGFs), such as acidic and basic fibroblast growth factors (aFGFs and bFGFs) in all forms, including native sequence FGF molecules from any animal species, including humans, and their functional derivatives, and VEGF-related molecules, such as PlGF, VEGF-B, and VEGF-C/VRP, including all native sequence forms from any animal species, including humans and other mammalian species, such as murine, bovine, equine, porcine, ovine, canine, or feline, and their functional derivatives. The definition specifically includes homo- and heterodimeric forms of these and related molecules, where dimerization is required for biological activity.

The phrase "factor that stimulates the production of an angiogenic factor", and grammatical equivalents thereof, are used in the broadest sense, and include compounds (native and variant polypeptides and peptides, small molecules, antibodies, etc.) that stimulate the expression of angiogenic factors, or receptors of angiogenic factors, regardless of the mechanism by which this stimulation is achieved. Such factors include, for example, platelet derived growth factors (PDGF) in all forms, transforming growth factors (TGF) in all forms, interleukin-1 (IL-1), interleukin-6 (IL-6), insulin-like growth factor (IGF) in all forms, heparin-binding epidermal growth factor, epidermal growth factor (EGF), adenosine, prostaglandins, or agents that activate protein kinase C, protein kinase A, or ras GTPase activating proteins. The designations of the listed angiogenic factors specifically include all naturally occurring forms from any animal species, including humans and other mammalian species, such as murine, bovine, equine, porcine, ovine, canine, or feline, and functional derivatives thereof.

Figure 1:
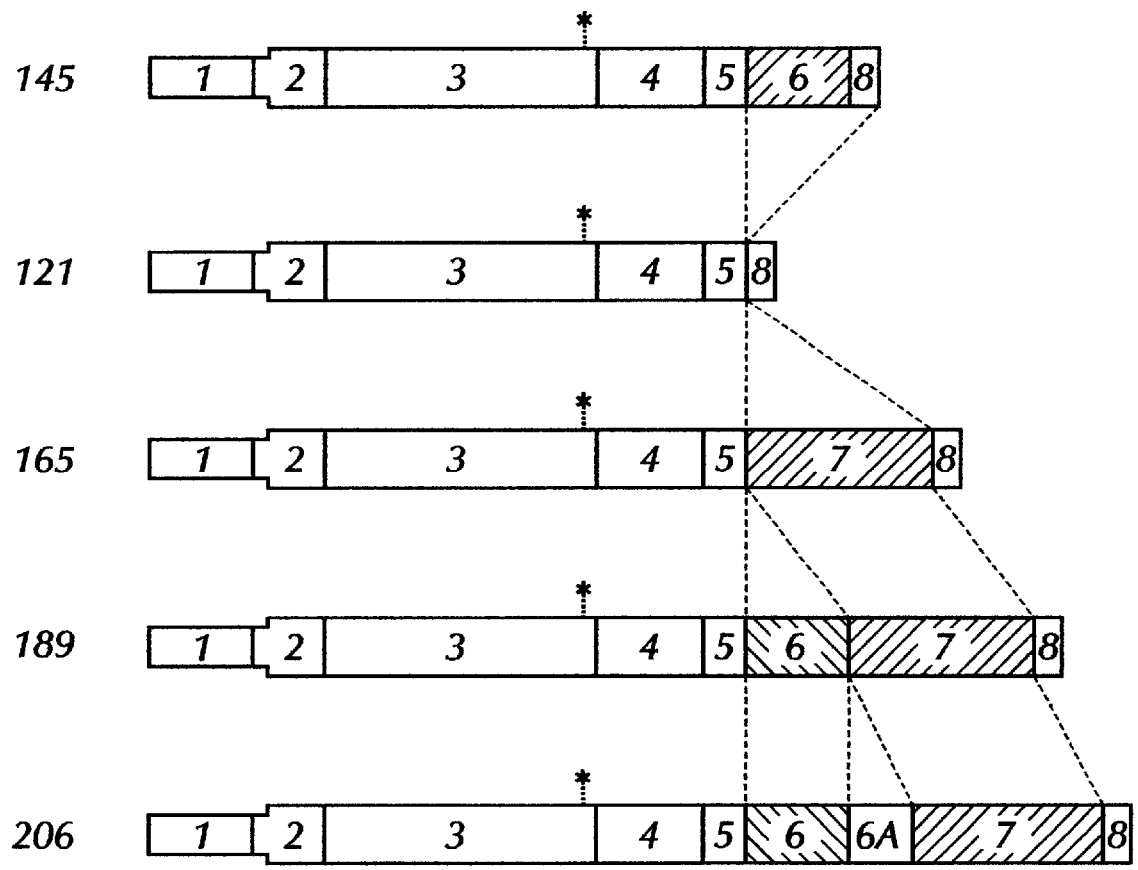
FIG. 1 is a schematic representation of the various forms of VEGF generated by alternative splicing of VEGF mRNA. The protein sequences encoded by each of the eight exons of the VEGF gene are represented by numbered boxes. The sequences encoded by exons 6 and 7 are rich in basic amino acid residues and confer the ability to interact with heparin and heparin-like molecules. Asterisks indicate N-linked glycosylation sites. Exon 1 and the first part of exon 2 (depicted by a narrower bar) encode the secretion signal sequence for the protein.

The term "vascular endothelial growth factor" or "VEGF" as used herein refers to any naturally occurring (native) forms of a VEGF polypeptide (also known as "vascular permeability factor" or "VPF") from any animal species, including humans and other mammalian species, such as murine, bovine, equine, porcine, ovine, canine, or feline, and functional derivatives thereof. "Native human VEGF" consists of two polypeptide chains generally occurring as homodimers. Each monomer occurs as one of five known isoforms, consisting of 121, 145, 165, 189, and 206 amino acid residues in length. These isoforms will be hereinafter referred to as hVEGF$_{121}$, hVEGF$_{145}$, hVEGF$_{165}$, hVEGF$_{189}$, and hVEGF$_{206}$, respectively. An "r" prefix before the designation of any VEGF species means that it has been produced by recombinant DNA technology. For example, rhVEGF$_{121}$, refers to recombinant human VEGF$_{121}$. Similarly to the human VEGF, "native murine VEGF" and "native bovine VEGF" are also known to exist in several isoforms, 120, 164, and 188 amino acids in length, usually occurring as homodimers. With the exception of hVEGF$_{121}$, all native human VEGF polypeptides are basic, heparin-binding molecules. hVEGF$_{121}$ is a weakly acidic polypeptide that does not bind to heparin. These and similar native forms, whether known or hereinafter discovered are all included in the definition of "native VEGF" or "native sequence VEGF", regardless of their mode a preparation, whether isolated from nature, synthesized, produced by methods of recombinant DNA technology, or any combination of these and other techniques. The term "vascular endothelial growth factor" or "VEGF" includes VEGF polypeptides in monomeric, homodimeric and heterodimeric forms. The definition of "VEGF" also includes a 110 amino acids long human VEGF species (hVEGF$_{110}$), and its homologues in other mammalian species, such as murine, bovine, equine, porcine, ovine, canine, or feline, and functional derivatives thereof. In addition, the term "VEGF" covers chimeric, dimeric proteins, in which a portion of the primary amino acid structure corresponds to a portion of either the A-chain subunit or the B-chain subunit of platelet-derived growth factor, add a portion of the primary amino acid structure corresponds to a portion of vascular endothelial growth factor. In a particular embodiment, a chimeric molecule is provided consisting of one chain comprising at least a portion of the A- or B-chain subunit of a platelet-derived growth factor, disulfide linked to a second chain comprising at least a portion of a VEGF molecule. More details of such dimers are provided, for example, in U.S. Pat. Nos. 5,194,596 and 5,219,739 and in European Patent EP-B 0 484 401, the disclosures of which are hereby expressly incorporated by reference. The nucleotide and amino acid sequences of hVEGF$_{121}$ and bovine VEGF$_{120}$ are disclosed, for example, in U.S. Pat. Nos. 5,194,596 and 5,219,739, and in EP 0 484 401. hVEGF$_{145}$ is described in PCT Publication No. WO 98/10071; hVEGF$_{165}$ is described in U.S. Pat. No. 5,332,671; hVEGF$_{189}$ is described in U.S. Pat. No. 5,240,848; and hVEGF$_{206}$ is described in Houck et al. *Mol. Endocrinol.* 5:1806–1814 (1991). Other VEGF polypeptides and polynucleotides have been described, including, for example, zvegf2 (PCT Publication No. WO 98/24811), and VRP (PCT Publication No. WO 97/09427), and are also encompassed by the term VEGF. For the disclosure of the nucleotide and amino acid sequences of various human VEGF isoforms see also Leung et al., *Science* 246:1306–1309 (1989); Keck et al., *Science* 246:1309–1312 (1989); Tisher et al., *J. Biol. Chem.* 266:11947–11954 (1991); EP 0 370 989; and PCT publication WO 98/10071. Forms of VEGF are shown schematically in FIG. 1. FIGS. 2–11 (SEQ ID NOs: 1–10) show the nucleotide and amino acid sequences of various VEGF species.

The phrase "functional derivative" is used to refer to fragments, amino acid sequence variants, glycosylation variants, and derivatives of a native sequence angiogenic factors, such as VEGF, as long as they retain the qualitative ability of a corresponding native molecule (e.g. VEGF) to prevent, reduce and/or reverse endothelial cell injury, preferably, but not necessarily, involving a mechanism other than the induction of new blood vessel formation (angiogenesis).

"Fragments" comprise regions within the sequence of a mature native polypeptide, and include, but are not limited to, proteolytic fragments, such as VEGF$_{110}$.

Functional derivatives specifically include amino acid sequence variants of native angiogenic factors. The term "amino acid sequence variant" or "variant" refers to angiogenic factor molecules with some differences in their amino acid sequences as compared to a corresponding native angiogenic factor, such as VEGF. Ordinarily, the variants will possess at least about 80% amino acid sequence identity, more preferably at least about 85% amino acid sequence identity, even more preferably at least about 90% amino acid sequence identity, most preferably at least about 95% amino acid sequence identity with a native angiogenic factor, such as a native sequence VEGF polypeptide. The amino acid sequence variants falling within the scope of this invention possess substitutions, deletions, and/or insertions at certain positions of the corresponding native molecule.

Substitutional variants are those that have at least one amino acid residue in the native sequence removed and replaced by a different amino acid. The substitutions may be single, where only one amino acid in the molecule has been substituted, or they may be multiple, where two or more amino acids have been substituted in the same molecule. Substantial changes in the activity of the native angiogenic factor (e.g. VEGF) molecule would be expected by substituting an amino acid with a side chain that is significantly different in charge and/or structure from that of the native polypeptide backbone and/or the charge or hydrophobicity of the molecule in the area of the substitution. Moderate changes in the activity of the angiogenic factor (e.g. VEGF) molecule would be expected by substituting an amino acid with a side chain that is similar in charge and/or structure to that of the amino acid present at the same site in the corresponding native angiogenic factor (e.g. VEGF). Substitutional variants of the VEGF molecules herein specifically include variants in which one or more native cysteine residues not required for biological activity are substituted by a different residue, preferably serine. Substitution of one or more cysteine residues reduces the opportunity for intra- and intermolecular disulfide bond formation, thereby rendering the molecule more stable. There are nine cysteine residues present in hVEGF$_{121}$, hVEGF$_{165}$, and the corresponding bovine and murine polypeptides. The most preferred substitutional variant is in which the ninth cysteine residue is substituted by serine. Amino acid substitutions can be accomplished by site specific mutagenesis of the DNA sequences described herein using well known techniques. See, e.g., Zoller and Smith (1982) *Nucleic Acids Research* 10:6487–6500. The amino acid sequence numbering system used herein for VEGF is based on the mature forms of the protein, i.e. the post-translationally processed forms. Accordingly, the residue numbered one in the human proteins is alanine, which is the first residue of the isolated, mature forms of these proteins.

Insertional variants are those with one or more amino acids inserted immediately adjacent to an amino acid at a particular position in the native VEGF molecule. Immediately adjacent to an amino acid means connected to either the alpha-carboxy or alpha-amino functional group of the amino acid. The insertion may be one or more amino acids. Ordinarily, the insertion consists of one or two conservative amino acids, i.e. amino acids similar in charge and/or structure to the amino acids adjacent to the site of insertion. Insertion of one or more amino acids with a charge and/or structure that is substantially different from the amino acids adjacent to the insertion site may also be desirable, if the biological properties are to be significantly altered. Insertional variants of angiogenic factors, e.g. VEGF, also include N-terminal extensions, in which one or more amino acids have been inserted between the initiating methionine and the native amino terminal amino acid.

Deletional variants are those with one or more amino acids in the native molecule, e.g. VEGF, removed. Deletional variants specifically include (VEGF) molecules with N- and/or C-terminal deletions compared with the corresponding native (VEGF) molecule, such as rhVEGF$_{121}$ as produced in *Pichia pastoris*, which is truncated by four N-terminal and one C-terminal amino acid residues compared to the native sequence.

VEGF variants with modifications in the C-terminal heparin binding domain, as disclosed in WO 98/36075, the disclosure of which is hereby expressly incorporated by reference, are specifically within the scope of the VEGF "amino acid sequence variants" of the present invention.

Functional derivatives also include glycosylation variants of native angiogenic factors, e.g. VEGF, the glycosylation pattern of which differs from the glycosylation pattern of a corresponding native angiogenic factor, e.g. VEGF, when expressed in the same host cell, under identical conditions. The VEGF glycosylation variants of the present invention, for example, may be unglycosylated, may be present in the form of heterodimers, in which one monomer is unglycosylated and the other in glycosylated, or the two monomers are differently glycosylated, or may lack one or more native glycosylation sites, and/or one or more glycosylation sites in addition to those present in a corresponding native VEGF polypeptide. Introduction of an N-linked glycosylation site requires a tripeptidyl sequence of the formula Asp-X-Ser or Asp-X-Thr, wherein X is any amino acid other than proline (Pro), which prevents glycosylation. If O-linked glycosylation is required, O-glycosidic linkage occurs between N-acetylgalactosamine, galactose, or xylose and one of several hydroxyamino acids, most commonly serine or threonine, or 5-hydroxyproline or 5-hydroxylysine residue placed in the appropriate region of the molecule. Expression of the DNA sequence encoding $hVEGF_{121}$ results in approximately 50% of the molecule modified at position 75 by N-linked glycosylation. There have been identified dimeric protein species in which both subunits are glycosylated or unglycosylated, and dimers in which one of the subunits is glycosylated and the other is unglycosylated. VEGF and other angiogenic factors, are produced in an unglycosylated form when expressed in E. coli. All of such glycosylation variants are specifically within the scope herein.

"Covalent derivatives" are also included within the meaning of functional derivatives. Covalent modifications may be introduced into the molecule by reacting targeted amino acid residues with an organic derivatizing agent that is capable of reacting with selected side chains or terminal residues. Further details of such covalent modifications are provided, for example, in U.S. Pat. No. 5,332,671, the disclosure of which is hereby expressly incorporated by reference.

"Sequence identity", is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", *Nucleic Acids Res.*, 25:3389–3402. The parameters are set to default values, with the exception of the Penalty for mismatch, which is set to −1.

The phrase "stimulators of angiogenic factors" and its grammatical variants are used to refer to factors that stimulate the production of angiogenic factors, or their receptors, and include, but are not limited to, platelet derived growth factors (PDGFs), transforming growth factors (e.g. TNF-$\alpha$ and -$\beta$), interleukin-1 (IL-1), interleukin-2 (IL-2), insulin-like growth factors (IGFs), heparin-binding epidermal growth factors (HBEGFs), epidermal growth factors (EGFs), adenosine, prostaglandins, agents that activate protein kinase C, protein kinase A, or ras GTPase activating proteins and their agonists.

The term "agonist" is used in the broadest sense and includes any molecule that mimics a biological activity of a native polypeptide angiogenic factor, such as VEGF, disclosed herein. Suitable agonist molecules specifically include agonist antibodies or antibody fragments, fragments or amino acid sequence variants of native angiogenic polypeptides, peptides and small organic molecules.

A "small molecule" is defined herein to have a molecular weight below about 500 daltons.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called $\alpha$, $\delta$, $\epsilon$, $\gamma$ and $\mu$, respectively. The subunit structures and three-dimensional configurations of different classes of immunoglobulins are well known.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies (see Kabat et al., *NIH Publ. No.*91-3242, Vol. I, pages 647–669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" to "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Clothia and Lesk, *J. Mol. Biol.* 196:901–917 [1987]). "Framework" or "FR" residues are those variable domain residues other than the hypervariable region residues as herein defined.

The term "antibody" is used herein in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include, for example, Fab, Fab', F(ab')$_2$, and Fv fragments; diabodies; linear antibodies (Zapata et al., *Protein Eng.* 8(10):1057–1062 [1995]); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 [1991] and Marks et al., *J. Mol. Biol.*, 222:581–597 (1991), for example.

The monoclonal antibodies herein specifically include "chimeric" antibodies in which the variable region of an antibody heavy or light chain is derived from one mammalian species (typically a rodent, e.g. mouse, rat or rabbit), while the constant region is derived from a different mammalian species (typically human), as well as fragments of such antibodies, so long as they exhibit the desired biological activity (U.S. Pat. No. 4,816,567; Morrison et al., *Proc. Natl. Acad. Sci. USA*, 81:6851–6855 [1984]).

"Humanized" forms of non-human (e.g., murine) contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. The humanized antibody optimally also will comprise at least a portion of an immunoglobulin constant region (Fc), typically that of a human immunoglobulin. For further details, see Jones et al., *Nature*, 321:522–525 (1986); and Reichmann et al., *Nature*, 332:323–329 [1988]. The humanized antibody includes a PRIMATIZED® antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

A "polynucleotide comprising sequences encoding an angiogenic factor" includes a polynucleotide comprising sequences encoding any of the above-mentioned angiogenic factors. Many such polynucleotides have been disclosed, including, for example, in the references mentioned above, wherein VEGF polypeptides are disclosed. The term encompasses polynucleotide sequences which hybridize under stringent hybridization conditions to the disclosed sequences, as long as the polypeptide encoded thereby is biologically active, i.e., it increases angiogenesis and/or increases vascular permeability.

The terms "vector", "polynucleotide vector", "construct" and "polynucleotide construct" are used interchangeably herein. A polynucleotide vector of this invention may be in any of several forms, including, but not limited to, RNA, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. A polynucleotide vector of this invention may be in the form of any of the delivery vehicles described herein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

"Under transcriptional control" is a term well-understood in the art and indicates that transcription of a polynucleotide sequence, usually a DNA sequence, depends on its being operably (operatively) linked to an element which contributes to the unification of, or promotes transcription.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, cats, cattle, horses, sheep, pigs, etc. Preferably, the mammal is human.

An "effective amount" is an amount sufficient to effect beneficial or desired clinical results. An effective amount can be administered in one or more administrations. For purposes of this invention, an effective amount of an angiogenic factor is an amount that is sufficient to palliate, ameliorate, stabilize, reverse, slow or delay the progression of the disease state. In a preferred embodiment of the invention, the "effective amount" is defined as an amount capable of preventing, reducing or reversing endothelial cell injury or injury to the surrounding tissues.

"Repair" of injury includes complete and partial repair, such as reduction of the injury that has already occurred, or partial reinstatement of the functionality of a tissue of organ.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment "Treatment" refers to both therapeutic treatment and prophylactic or preventative measures. Those in need of treatment include those already with the disorder as well as those in which the disorder is to be prevented. In a preferred embodiment, "treatment" in the context of the present invention is an intervention performed with the intention of preventing the development of endothelial cell injury or injury to the surrounding tissues in patients at risk and/or or reducing or reversing endothelial cell injury or injury to the surrounding tissue in the patients treated.

"Palliating" a disease means that the extent and/or undesirable clinical manifestations of a disease state are lessened and/or time course of the progression is slowed or lengthened, as compared to a situation without treatment.

Administration "in combination with" one or more further therapeutic agents includes simultaneous (concurrent) and consecutive administration in any order.

The phrase "hemolytic-uremic syndrome" or "HUS" is used in the broadest sense, and includes all diseases and conditions characterized by thrombotic microangiopathic hemolytic anemia and variable organ impairment, irrespective of whether renal failure is the predominant feature. The disease is particularly frequent in childhood, where it is the most common cause of acute renal failure. However, the phrase, as defined herein, specifically covers a syndrome, typically observed in adults, that is also referred to as thrombotic thrombocytopenic purpura (TTP) and is generally characterized by the predominance of thrombocytopenia and neurologic impairment, but has thrombotic microangiopathy as the underlying pathologic lesion.

The term "focal glomerulosclerosis" is used to refer to a condition associated with microvascular angiopathy and characterized by the presence of focal sclerosing lesions of the glomeruli of kidney, regardless of the underlying cause. Focal glomerulosclerosis is common and used as an indicator of poor prognosis in idiopathic nephrotic syndrome, but may also arise secondary to a wide variety of other glomerular and multisystem disorders, associated with infections (e.g. human immunodeficiency virus (HIV) infection), drugs and medications (e.g. drug abuse, NSAID, analgesic abuse), reduced renal mass (e.g. inoligonephronia, unilateral renal agenesis, renal dysplasia, etc.), or processes that directly damage epithelial cells or induce hemodynamic alterations favoring glomerular sclerosis (e.g. diabetes mellitus, hypersensitive arteriosclerosis, postinflammatory or postnecrotic scarring).

The term "amyloidosis" refers to a diverse family of chronic infiltrative disorders characterized by the presence of extracellular deposits of insoluble fibrillar proteins. Amyloidosis frequently results in the development of renal nephrotic syndrome often followed by progressive renal insufficiency.

The term "glomerulonephritis" or "GN" is used in the broadest sense to include all primary glomerular diseases in which the structure or function of the glomerular capillary network is disturbed as a result of processes that are largely limited to the kidney. The term specifically includes acute glomerulonephritis, rapidly progressive glomerulonephritis, and chronic glomerulonephritis, regardless of the causative factors and underlying pathology.

The term "diabetes" is used in the broadest sense and specifically includes insulin-dependent diabetes mellitus (IDDM, type I diabetes), and non-insulin-dependent diabetes mellitus (NIDDM, type II diabetes). Patients with IDDM have increased mortality because of vascular complications, partially due to endothelial cell injury.

The phrase "systemic lupus erythematosus" or "SLE", is a secondary glomerular disease, in which renal involvement is well documented. It is commonly believed that most patents with SLE have glomerular Ig and complement component deposits, and display glomerular lesions, often exhibiting chronic changes, such as tubule atrophy, interstitial fibrosis, glomerular sclerosis, fibrous crescents, adhesions and arteriosclerosis.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Modes of Carrying Out the Invention

The present invention concerns methods and compositions for the prevention and/or repair of injury to blood vessels by the administration of angiogenic factors, their agonists, or factors that stimulate the production of angiogenic factors. In a particular embodiment, the invention concerns methods and compositions for the prevention and/or repair of vascular injury associated with microvascular angiopathy and, in particular, thrombotic microangiopathy. The invention further concerns methods and compositions for the prevention and/or repair of injury to nonvascular tissue associated with injury to blood vessels serving such tissue via administration of angiogenic factors, their agonists, or factors that stimulate the production of angiogenic factors.

A. Angiogenic factors

Exemplary angiogenic factors have been listed hereinbefore. In general, an angiogenic factor can be a biological or chemical compound such as a simple or complex organic or inorganic molecule, a peptide, or a protein. A vast array of compounds can be synthesized, for example, oligopeptides, and synthetic inorganic and organic compounds based on various core structures, and these are also included. Preferred angiogenic factors for the purpose of the present invention include, but are not limited to, VEGF, aFGF, and bFGF, as hereinbefore defined.

B. Amino acid sequence variants of native angiogenic factors

Variations in the amino acid sequence of native angiogenic factors, such as native VEGF polypeptides, involve substitution, deletion and/or insertion of one or more amino acids in the native polypeptide sequence. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in any assay of high blood pressure, such as the assay described in the Examples below.

In a preferred group of amino acid sequence variants, one ore more cysteine residues in the VEGF structure is replaced by another amino acid. Such substitution reduced the opportunity for intermolecular and intramolecular disulfide bond formation, thereby rendering the molecule more stable. There are nine cysteine residues present in hVEGF120, hVEGF165, and in the respective bovine homologues. Of these, eight are conserved with PDGF. Accordingly, the most preferred analog is in which the ninth cysteine residue is substituted by serine. This cysteine residue is presented at position 160 of hVEGF165 and position 116 of hVEGF 121, and the corresponding positions of the bovine forms. Some additional information about variant forms of VEGF molecules is provided in U.S. Pat. No. 5,332,671. Specifically included herein are the variant VEGF molecules described in PCT Publication WO 98/36075, the disclosure of which is expressly incorporated by reference. Such VEGF molecules contain modifications in the C-terminal heparin binding domain that are described to result in functional modification of the pharmacokinetic profile, and yield molecules having a reduced clearance rate compared with the corresponding heparin-binding native VEGF molecule. Preferred embodiments include the replacement of positively charged amino acids with negatively charged or neutral amino acids within the heparin-binding domain of a heparin-binding VEGF species. In addition, VEGF variants in which portions of the C-terminal heparin-binding domain are deleted are included within the scope of the present invention. The variations can be made using methods known in the art such as oligonucleotide-mediated (site-directed) mutagenesis, alanine scanning, and PCR mutagenesis, or can occur as a result of inherent properties of the host selected from recombinant production. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene, 34:315* (1985)], restriction selection mutagenesis [Wells et al., *Philos. Trans. R. Soc. London SerA,* 317:415 (1986)] or other known techniques can be performed on the cloned DNA to produce the DNA encoding a VEGF variant.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081–1085 (1989)]. Alanine is also typically preferred because it is the most common amino acid. Further, it is frequently found in both buried and exposed positions [Creighton, *The Proteins*, (W. H. Freeman & Co., N.Y.); Chothia, *J. Mol. Biol.,* 150:1 (1976)]. If alanine substitution does not yield adequate amounts of variant, an isoteric amino acid can be used.

C. Agonists of angiogenic factors

Antibodies

Some drug candidates according to the present invention are agonist antibodies that mimic the ability of an angiogenic factor, preferably a VEGF, to prevent and/or repair vascular injury or injury to nonvascular tissue associated with injury to blood vessels serving such tissue.

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular angiogenic factor used, such as VEGF. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', F(ab')$_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human immunoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences [Jones et al., *Nature*, 321:522–525 (1986); Riechmann et al., *Nature*, 332:323–329 (1988)].

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. In addition, human antibodies can be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may be bispecific, in which one specificity is for an angiogenic factor, and the other specificity for another protein, such as, a second angiogenic factor, or a different epitope of the same angiogenic factor.

Screening assays for drug candidates

Screening assays for drug candidates are designed to identify agonists, such as antibody or small molecule agonists, of the angiogenic factors (e.g. VEGF) used in the methods and compositions of the present invention. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

Preferably, the biological activity of drug candidates is tested in appropriate animal models of the condition to be treated. The recognition that angiogenic factors find utility in the treatment of thrombotic microagiopathy (TMA) is based on studies performed in a rat model of hemolytic uremic syndrome (HUS). Until recently, there have not been good animal models of TMA or HUS. This is in part because the major toxin causing HUS in man, which is the verotoxin (Shiga toxin) produced by *E. coli* O157, appears to cause endothelial damage by binding to the G3b receptors which are present in human glomerular endothelium but which are not present in rodent kidneys. Remuzzi and Ruggenenti, *Kidney Int.* 47:2–19 (1995). Although there have been a few reports of models of glomerular endothelial injury induced by lectins, cyclosporine, or other agents, none of these have resulted in a clinical syndrome characteristic of HUS in man. Nangaku et al., *Curr. Opin. Nephrol. Hypert.* 7: 457–462 (1998).

Recently, a new model of renal TMA has been developed with many features of HUS by passive administration of heterologous anti-rat glomerular endothelial cell (anti-GEN) antibody to rats. See, Nangaku et al., *Kidney Int.* 52: 184–194 (1997); Nangaku et al., *J. Am. Soc. Nephr.* 9:590–497 (1998); Nangaku et al., *Kidney Int.* 52:1570–1578 (1997). The antibody was generated by immunizing a goat with whole rat glomerular endothelial cells that has been growth in culture, and resulted in high titers of antibody with reactivity to glomerular and, to a lesser extent, other microvascular and macrovascular endothelial cells in the rat. Infusing this antibody into the renal artery of rats (range 20–80 mg/kg) results in glomerular and microvascular endothelial cell injury and apoptosis, focal detachment, platelet activation and localization, and tubular injury. The rats have a significant fall in circulating platelet counts and hematocrit, and show microangiopathic changes on peripheral blood smear. If the control non-perfused kidney is surgically removed at the time of the infusion, then the rats will develop rapid onset of renal failure (Nangaku et al., *Kidney Int.* 52: 184–194 (1997)). This animal model was used for testing $hVEGF_{121}$ but is equally suitable for testing the biological activity of further angiogenic factors, including VEGF variants, their agonists, and factors that stimulate the production of angiogenic factors. Further details of using the rat model of HUS will be apparent from the examples provided hereinbelow.

Therapeutic targets

As noted before, microvascular injuries occur in a variety of disorders characterized by injury to smaller vessels and subsequent dysfunction of the tissue in which those blood vessels are located. The injury is often associated with endothelial cell death and the presence of products of coagulation or thrombosis. The agent of injury may be a toxin, immune factor, an infectious agent, a metabolic or physiological stress, a component of the humoral or cellular immune system, or may be as yet unidentified. Thrombotic microangiopathies may also occur as a complication of pregnancy (eclampsia), malignant hypertension, etc. Such microvascular injuries (including thrombotic microangiopathies) may develop in various organs, such as kidney, heart, and lungs.

The present invention is particularly directed to the treatment (including prevention) of injury to blood vessels and to the treatment (including prevention) of injury to tissues containing such blood vessels, in conditions where the endothelial cell injury is mediated by known or unknown toxins, such as occurs in hemolytic uremic syndrome (HUS), toxic shock syndrome, exposure to venoms, or exposure to chemical, medicinal, or immunological toxins, and in conditions where the endothelial cell injury is mediated by hypertension.

The invention further concerns the treatment (including prevention) of kidney diseases associated with injury to, or atrophy of, the vasculature of the glomerulus and interstitium.

The invention also concerns the treatment (including prevention) of injury to the endothelium of blood vessels, and for the treatment (including prevention) of injury to tissues containing such injured blood vessels in diseases associated with hypercoagulable states, platelet activation or aggregation, thrombosis, or activation of proteins of the clotting cascade, or in activation of coagulation or platelet aggregation such as preeclampsia, thrombotic thombocytopenic purpura (TTP), disseminated intravascular coagulation, sepsis, pancreatis.

The invention also provides methods for the treatment (including prevention) of injury to blood vessels or injury to the surrounding tissue adjacent to injured blood vessels arising as a result of diminished blood flow due to decreased blood pressure, or full or partial occlusion of the blood vessel, due to atherosclerosis, thrombosis, mechanical trauma, vascular wall dissection, surgical dissection, or any other impediment to normal blood flow or pressure. Specifically, the invention provides methods for the treatment (including prevention) of acute renal failure, myocardial infarction with or without accompanying thrombolytic therapy, ischemic bowel disease, transient ischemic attacks, and stroke.

The invention also provides methods for the treatment (including prevention) of hypoxia or hypercapnia or fibrosis arising from injury to the endothelium of the lungs occasioned by injurious immune stimuli, toxin, exposure, infection, or ischemia, including but not limited to acute respiratory distress syndrome, toxic alveolar injury, as occurs in smoke inhalation, pneumonia, including viral and bacterial infections, and pulmonary emboli.

The invention further provides methods and means for the treatment )including prevention) of pulmonary dysfunction arising from injury to the pulmonary endothelium, including disorders arising from birth prematurity, and primary and secondary causes of pulmonary hypertension.

The methods disclosed herein can also be used for the treatment of wounds arising from any injurious breach of the dermis with associated vascular injury.

The invention also provides methods for the treatment (including prevention) or injury to the endothelium and blood vessels, and for the treatment (including prevention) of injury to tissues containing injured blood vessels, due to injurious immune stimuli, such as immune cytokines, immune complexes, proteins of the complement cascade, including but not restricted to diseases such as vasculitis of all types, allergic reactions, diseases of immediate and delayed hypersensitivity, autoimmune diseases.

The methods of the present invention further useful in the preservation or enhancement of function of organ allografts, including but not restricted to transplants of kidney, heart, liver, lung, pancreas, skin, bone, intestine, and xenografts.

Specific kidney diseases that may be treatable by using the methods of the present invention include HUS, focal glomerulosclerosis, amyloidosis, glomerulonephritis, diabetes, SLE, and chronic hypoxia/atrophy.

Delivery vehicles comprising polynucleotides encoding an angiogenic factor

The present invention also provides delivery vehicles suitable for delivery of a polynucleotide encoding an angiogenic factor into cells (whether in vivo, ex vivo, or in vitro). Generally, a polynucleotide encoding an angiogenic factor will be operably linked to a promoter and a heterologous polynucleotide. A polynucleotide encoding an angiogenic factor can be contained within a cloning or expression vector, using methods well known in the art, or within a viral vector. These vectors (especially expression vectors) can in turn be manipulated to assume any of a number of forms which may, for example, facilitate delivery to and/or entry into a target cell. Delivery of the polynucleotide constructs of the invention to eukaryotic cells, particularly to mammalian cells, more particularly to distal tubule cells of the kidney, can be accomplished by any suitable art-known method. Delivery can be accomplished in vivo, ex vivo, or in vitro.

The invention provides methods and compositions for transferring such expression constructs into cells, especially in vivo for performing the methods of the present invention. It is also an object of the invention to provide compositions for the treatment (including prevention) of the conditions listed above by providing for the prevention or repair of the underlying vascular injury and/or the associated damage to non-vascular tissues.

Delivery vehicles suitable for incorporation of a polynucleotide encoding an angiogenic factor of the present invention for introduction into a host cell include non-viral vehicles and viral vectors. Verma and Somia (1997) *Nature* 389:239–242.

A wide variety of non-viral vehicles for delivery of a polynucleotide encoding an angiogenic factor are known in the art and are encompassed in the present invention. A polynucleotide encoding an angiogenic factor can be delivered to a cell as naked DNA (U.S. Pat. No. 5,692,622; WO 97/40163). Alternatively, a polynucleotide encoding an angiogenic factor can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle can be a microparticle. Mixtures or conjugates of these various substances can also be used as delivery vehicles. A polynucleotide encoding an angiogenic factor can be associated non-covalently or covalently with these various forms of delivery. Liposomes can be targeted to a particular cell type, e.g., to a glomerular epithelial cell.

Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) *Science* 272:263–267.

Non-viral delivery vehicles comprising a polynucleotide encoding an angiogenic factor can be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field.

Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA.* 74:3471; and Faller et al. (1984) *J. Virol.* 49:269).

For in vivo delivery, the delivery vehicle(s) can be introduced into an individual by any of a number of methods, each of which is familiar in the art.

Pharmaceutical compositions

Pharmaceutical compositions for use in the methods of the present invention can comprise a polynucleotide encoding an angiogenic, or, alternatively, pharmaceutical compositions can comprise an angiogenic factor itself.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

Compositions comprising an angiogenic factor or an angiogenic factor-encoding polynucleotide can also be formulated as pharmaceutically acceptable salts (e.g., acid addition salts) and/or complexes thereof. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intraperitoneal, subcutaneous, and intramuscular, oral, topical, or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions comprising an angiogenic factor or a polynucleotide encoding an angiogenic factor can be formulated for a variety of modes of administration, including systemic and topical or localized administration. Techniques and formulations generally may be found in *Remington's Pharmaceutical Sciences,* 18th Edition, Mack Publishing Co., Easton, Pa. 1990. See, also, Wang and Hanson *"Parenteral Formulations of Proteins and Peptides: Stability and Stabilizers", Journal of Parenteral Science and Technology,* Technical Report No. 10, Supp. 42-2S (1988). A suitable administration format can best be determined by a medical practitioner for each patient individually.

For systemic administration, injection is preferred, e.g. intramuscular, intravenous, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Useful buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, the compounds can be administered orally. For oral administration, the compounds are formulated into conventional oral dosage forms such as capsules, tablets and tonics.

Systemic administration can also be transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

For oral administration, the molecules are formulated into conventional oral administration dosage forms such as capsules, tablets, and liquid preparations.

For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg, preferably 1 and 20 mg/kg of the individual to be treated.

For use by the physician, the compositions are provided in dosage unit form containing an amount of an angiogenic factor.

The following examples are provided to illustrate but not limit the invention. All references cited throughout the specification, including the examples, are hereby expressly incorporated by reference.

EXAMPLE 1

Reduction of Acute Mortality by VEGF in Experimental TMA

Sprague Dawley rats (200 g or larger) were anesthetized with equithesin (a combination of ketimine, acepromazine and xylazine), and then underwent a laparotomy with removal of the left kidney. The aorta was then isolated and ties placed around the aorta above and below the ostium of the right renal artery. A tie was then placed around the superior mesentic artery, which is opposite the right renal artery, and blood flow to the right kidney was transiently stopped by the placement of stainless steel clips. The superior was perfused with phosphate buffered saline (0.5 ml) to flush the blood out of the kidney, followed by 1 ml of 40 mg/kg of a goat anti-rat glomerular endothelial cell antibody (anti-GEN IgG, described in Nangaku et al., *Kidney Int.* 52:1570–1578 (1997); see also Nangaku et al., *Kidney Int.* 52:182–194 (1997) and Nangaku et al., *Curr. Opin. Nephrol. Hypertens* 7:457–462 (1998), describing the model). Following the perfusion, renal blood flow was restored (total ischemia time always less than 10 min) and the needle removed and bleeding stopped with gelfoam. The wound was then closed and the animal allowed recovering under a heated lamp. Beginning one hour after the infusion of the antibody, the rats were injected in a blinded manner either hVEGF$_{121}$ (50 g/kg) or vehicle subcutaneously (s.c.) every 12 hours. In this study, the endpoint was mortality during the first four days, which was assumed to be due to the severe renal failure given the marked rise in BUN that occurs in the first 24 hours with this dose (Nangaku et al., *Curr. Opin. Nephrol. Hypert.* 7:457–462 (1998).

The results are shown below.

|  | Total mortality |  |
|---|---|---|
| Control (n = 8) | 7/8 (87.5%) | p = 0.25 |
| VEGF treatment (n = 8) | 5/8 (62%) |  |

These results provide strong and suggestive evidence that VEGF infusion may have the ability to reduce acute mortality in experimental TMA.

EXAMPLE 2

Reduction of Cortical Necrosis by VEGF Infusion in Experimental TMA

We have examined the effect of hVEGF$_{121}$ to prevent cortical necrosis in the animal model described in Example 1. Because of the severity of the diseases and the high mortality in control rats in Example 1, the present study was modified such that the nonperfused kidney was not removed (which prevents the development of renal failure due to the presence of a normal kidney). The experiment was otherwise performed essentially as described in Example 1, except that a higher dose of anti-glomerular endothelial cell antibody (anti-GEN IgG, 80 mg/kg) was administered by selective perfusion of the right kidney through the superior mesentric artery. Earlier studies with this model have demonstrated that both cortical and medullary infarction would occur when a high dose of anti-GEN antibody was infused. We wondered if the early administration of VEGF could prevent this complication. We, therefore, injected rhVEGF$_{121}$ (50 μg/kg) beginning 1 hour after injection of the 80 mg/kg dose of anti-GEN antibody. The control animals received PBS. The administration was performed subcutaneously, twice a day with 12-hr interval at different sites, and continued for 7 days. Rats were anesthetized and underwent renal biopsies 10 minutes, 4 days and 7 days after the perfusion. Tissue was fixed in methylcarnoy's fixative, paraffin embedded, sectioned (4-μm) and stained with periodic acid/Schiff reagent (PAS), or processed for immunostaining of the following antigens: α-smooth muscle actin (α-SMA, a marker of smooth muscle cells) with 1A4 (Sigma Chemical Co); endothelial cells with the RECA-1 antibody (Harlan Bioproducts, see also Nangaku et al., *Kidney Int.* 52:182–194 (1997)); and endothelial nitric oxide synthase (eNOS, NOS III) with mouse anti-eNOS antibody (Transduction Labs, Lexington, Ky., as previously described in Lombardi et al., *Hypertension* 33:1013–1019 (1999)). To confirm the glomerular endothelial binding of the injected anti-GEN IgG antibody, immunofluorescence was performed on 4-μm frozen tissue sections obtained 10 minutes after IgG perfusion using rabbit anti-goat IgG (Cappel, Organ Teknika Corp., Durham, N.C.) (Nangaku et al., *Kidney Int.* 52: 182–194 (1997), supra). Morphometric analysis of RECA-1 positive glomeruli density and α-SMA positive vessels was performed using computer-assisted image analysis software (Optimas, v. 6.2, Media Cybernetics, Silver Springs, Md.) and digitalized images. The % area occupied by necrotic tissue was measured at 2.5× on whole cortex and medulla of each biopsy by measuring the percent necrotic areas in PAS-stained sections using the Optimas system described above. The number of RECA-1positive glomeruli and SMA positive vessels was quantified per 5× field in the cortical and juxtamedullary regions and mean number per mm$^2$ was calculated.

Results

Figure 13A:
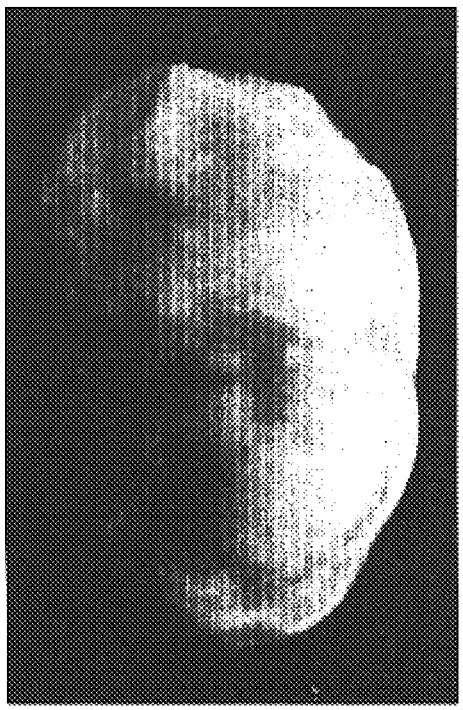
FIGS. 13A–13D shows the appearance of kidney in a mouse model of renal microvascular endothelial injury in the absence (panels A and B) and presence (panels C and D) of rhVEGF$_{121}$. Panels A and C are pictures of the whole kidney, panels B and D show kidney sections.
Figure 13B:
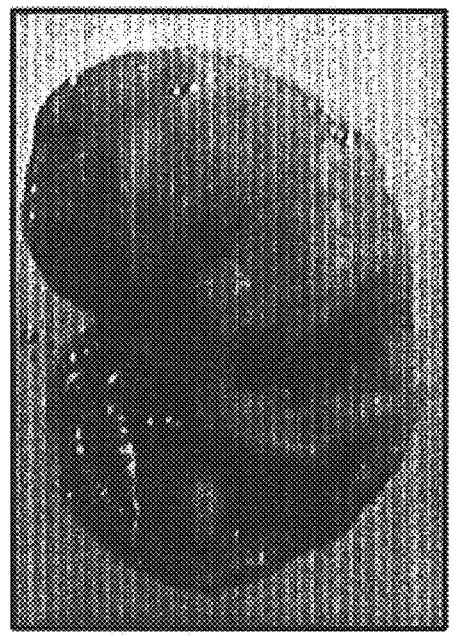
Figure 14A:
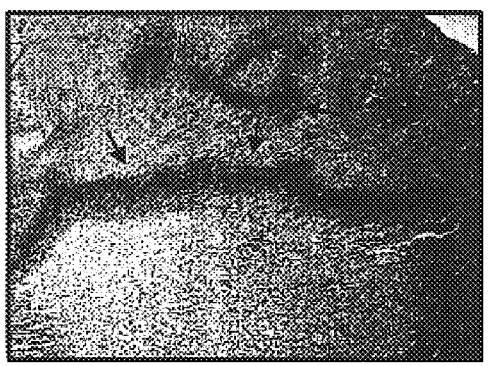
FIGS. 14A–14E shows the results of histological study of paraffin-embedded, and fixed renal tissue sections, stained with the periodic acid/Schiff reagent (PAS) at low and high power, in the absence (panels A–C) and presence (panels D and E) of rhVEGF$_{121}$.
Figure 14B:
Figure 14C:
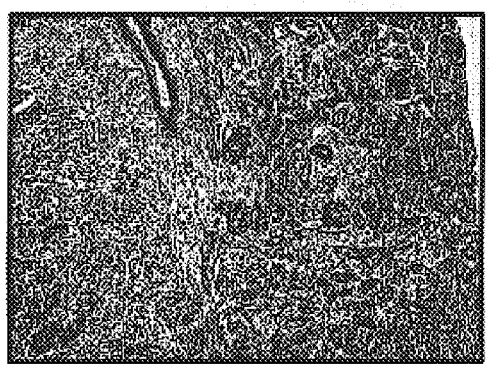

At day 7, surface of the perfused kidneys was covered with yellowish white areas with intervening reddish area in VEGF non-treated group (FIG. 13A). No macroscopic abnormality was observed in non-perfused left kidney (not shown). Cut surface showed patchy yellowish shite areas distributed in cortex as well as in medulla (FIG. 13B). Cortex immediately under the capsule was relatively preserved. Histologically, there were various sizes of typical necrotic areas (FIG. 14A, arrow), which have central dead zone composed of necrotic tissues with nuclear loss in glomeruli and tubules (FIG. 14B), peripheral dead zone with glomerular and tubular nuclear loss and polymorphnuclear cell infiltration (FIG. 14B, arrow), and marginal zone with various degrees of necrosis, tubular regeneration and fibrosis (FIG. 14C).

Figure 13C:
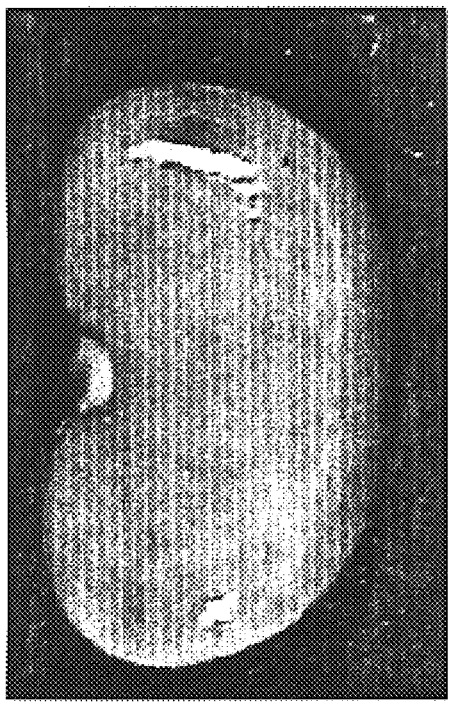
Figure 13D:
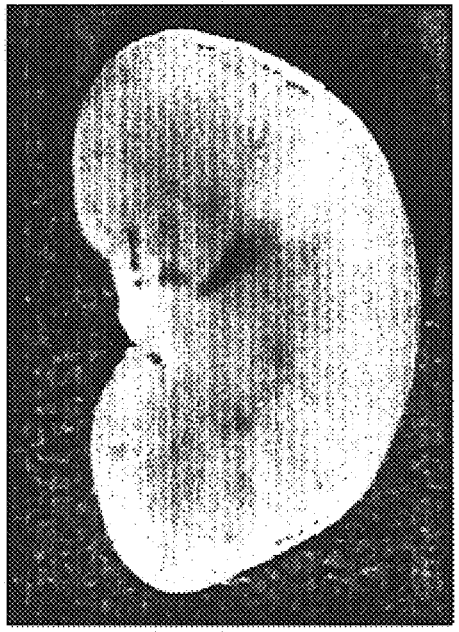
Figure 14D:
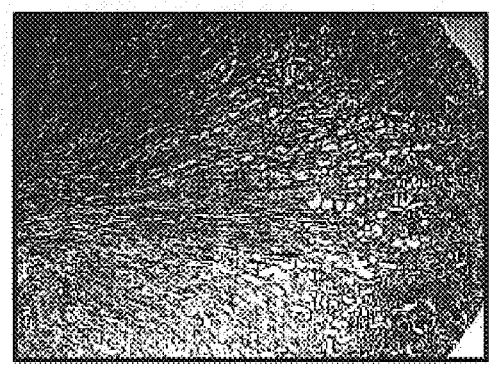
Figure 14E:
Figure 15A:
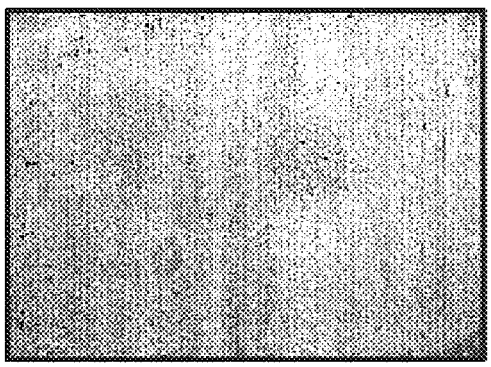
FIG. 15A shows the results of α-smooth muscle actin (α-SMA) staining in tissue sections of the cortex of non-VEGF treated rats.
Figure 15B:
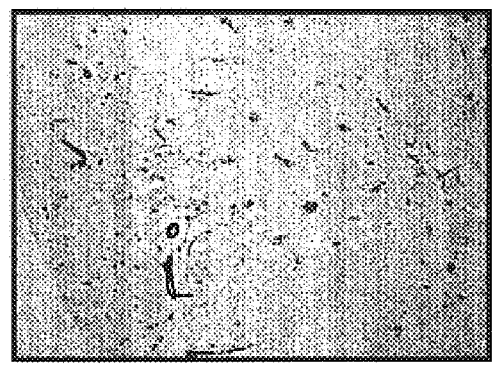
FIG. 15B shows the results of α-SMA staining in tissue sections of the cortex of VEGF treated rats, and illustrates that VEGF treatment preserves large blood vessels.

Systemic administration of rhVEGF$_{121}$ for 7 days after anti-GEN IgG perfusion resulted in elimination of macroscopic evidence of necrosis in most rats (FIGS. 13C, D). In cut surface, necrotic areas were distributed mainly in medulla. Histological study showed that necrotic areas became less than 5% in cortex and decreased to 36% in medulla (FIG. 14D, Table 1). (In non-necrotic areas, about half of the glomeruli showed mesangial expansion, while the remaining half looked grossly normal.) Dilation and atrophy of tubules were prominent in the outer medulla (FIG. 14E). There was no difference in deposition of the pathogenic goat IgG between two groups (data not shown).

rhVEGF$_{121}$ administration has been found to preserve renal vasculature. At day 7, the number of glomeruli with intact endothelial lining was larger in the VEGF-treated group than in the control group (Table 1, FIG. 15E). In the control group, α-smooth muscle actin (α-SMA) positive vessels (indicating arterioles) were rarely observed in the medulla (FIG. 15A), however, large number of α-SMA positive vessels were distributed in vascular bundles in the VEGF-treated group (FIG. 15B). α-SMA positive vessels were relatively preserved in superficial cortex in VEGF non-treated group (FIG. 15A) but still there was a significant decrease in the number of α-SMA positive vessels, when compared to the VEGF-treated group (Table 1, FIG. 15B).

Figure 15C:
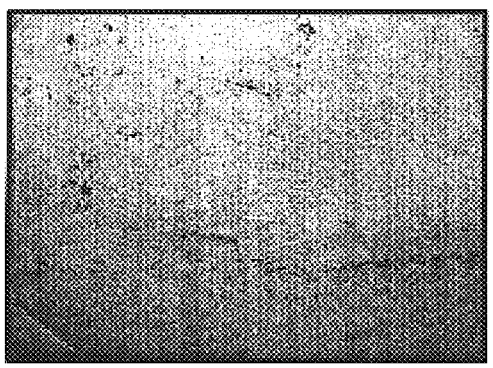
FIG. 15C shows the results of eNOS staining in tissue sections of the medulla of non-VEGF treated rats.
Figure 15D:
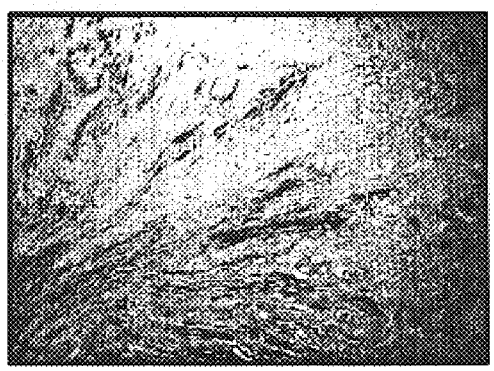
FIG. 15D shows the results of eNOS staining in tissue sections of the medulla of VEGF treated rats. In contrast to the non-VEGF treated animals (15C), a large number of eNOS positive vessels were distributed in vascular bundles in the VEGF-treated group.
Figure 15E:
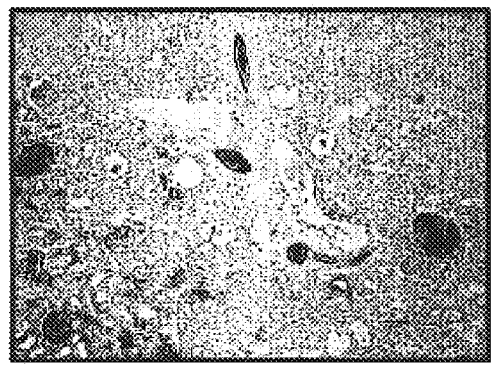
FIG. 15E shows the results of RECA-1 staining in the glomeruli of VEGF treated rats.

We have also monitored the expression of endothelial nitric oxide synthase (eNOS) by immunostaining and/or Western at the 4-hour time point. In the group receiving anti-GEN antibody only, the eNOS was localized in the endothelium of some arteries, arterioles, and glomeruli in the cortex and there was little staining of eNOS in the medulla (FIG. 15C). In VEGF-treated rats, eNOS was widely distributed in glomerular and vascular endothelial cells as well as in tubular epithelial cells and vascular bundles in the medulla (FIG. 15D). We also examined the number of PCNA-positive cells in the glomeruli, which did not show significant difference between two groups (Table 1).

TABLE 1

|  | Anti-GEN | Anti-GEN + VEGF (n = 6, day 7) |
| --- | --- | --- |
| Cortical necrosis (%) | 46 ± 10 | 5 ± 3* |
| Medullary necrosis (%) | 81.3 ± 19.0 | 36.5 ± 10.8* |
| Nephron number (/mm$^2$) | 3.3 ± 1.3 | 5.9 ± 0.3* |
| α-SMA positive vessels in cortex | 9 | 15* |
| PCNA positive cells (/glomerulus) | 2.4 ± 1.0 | 2.5 ± 1.8* |

* $p < 0.05$. Renal infarction was measured by computer image analysis of the kidney. Glomerular number was calculated as the number of glomeruli per mm$^2$ within the viable portion of the kidney.

In this model of HUS, injury to the endothelium is mediated by the localization of activated complement to the endothelial membrane induced by the binding of specific antibody. To determine if VEGF might exert a protective effect against injury induced by circulating toxins, such as complement proteins, we examined the effect of VEGF$_{121}$ in vitro, in a model of cell death. Human umbilical vein endothelial cells (HUVEC) were plated in tissue culture wells in routine culture medium supplemented by 5% fetal bovine serum (FBS). The cells were then placed in serum free medium, which induced some cell death as determined by activation of caspase-3C (Table 2). As shown in Table 2, exposure of cells to 10% zymosan-activated rabbit serum (zymosan activates the complement cascade) demonstrated increased cell death. Cells exposed to VEGF at 50 ng/ml for 4 hrs or 14 hrs prior to exposure to zymosan-activated serum showed complete protection against complement-mediated augmentation of cell injury.

TABLE 2

| Treatment | % increase in cell death |
| --- | --- |
| Activated complement | 75% |
| VEGF (4 hrs) + activated complement | 0% |
| VEGF (24 hrs) + activated complement | 0% |

Discussion

The present study demonstrates that administration of rhVEGF$_{121}$ leads to the reduction of endothelial cell apoptosis, the preservation of vascular structures including glomerular capillary and protection of renal necrosis in a HUS-like model induced by anti-GEN antibody. We also showed that rhVEGF$_{121}$ inhibited endothelial cell injury induced by activated complement in vitro. Therefore, the protective effect of VEGF on renal injury is attributed to the prevention of endothelial cell injury in this model. It has been reported earlier that VEGF can prevent cultured endothelial cell apoptosis induced by serum starvation (Gerber et al., *J. Biol. Chem.* 273:30336–30343 (1998)) or TNF-α (Spyridopoulos et al., *J. Mol. Cell Cardiol.* 29:1321–1330 (1997) [erratum published in *J. Mol. Cell Cardiol.* 30:897 (1998)). VEGF inhibition resulted in endothelial cell apoptosis and impairment of development or various organs in neonates (Gerber et al., *Development* 126:1149–1159 (1999)). However, prior to the present work, in adult the protective effect of VEGF on endothelial cells has been shown only in tumor tissues. This is the first study that indicates the protective effect of VEGF on non-tumor vessels in adults. Another important known action of VEGF is angiogenesis, and VEGF has been tested as a potential therapeutic factor for ischemic diseases in adults. In the present study, however, the number of PCNA positive cells did not show significant difference between two groups at day 4 or day 7. In addition, it has been reported that at least two weeks are required to observe an increase in capillary density and blood flow in the ischemic tissue treated with VEGF (Takeshita et al, *J. Clin. Invest.* 93:662–670 (1994)). Thus, it is unlikely to ascribe the improvement of renal necrosis at day 7 to the enhancement of microvascular regeneration. While we are not intended to be bound by any particular theory, a possible mechanism of the renal protective effect of VEGF is associated with its vasodilatory, anti-platelet and/or anti-coagulation actions mediated by NO. We have previously observed the transient enhancement of glomerular VEGF and eNOS immunostaining in this model at 4–24 hours after the induction of disease (Nangaku et al., *Kidney Int.* 52:182–194 (1997)). Glomerular VEGF mRNA level also rose transiently at 24 hour and became below normal at day 7 (unpublished observation). It could be possible, therefore, to consider the elevation of VEGF and NO levels as a self-defense mechanism against the glomerular endothelial injury, which is insufficient to block the progression of injury. Administration of exogenous VEGF may be a reinforcement of an endogenous defense mechanism.

EXAMPLE 3

VEGF Stimulates Remodeling and Tissue Repair in a Model of TMA

Essentially in the same animal model described in Example 1, we tested the hypothesis that VEGF might be beneficial in rats with established TMA. TMA was induced in rats by the selective right renal artery perfusion of a lower dose of anti-GEN IgG (30 mg/kg). Twenty-four hours later, rats received rhVEGF$_{121}$ (50 μg/kg, b.i.d) or vehicle (control) daily until day 14. In order to assess the effect of VEGF treatment on kidney function in this unilaterally perfused model, the nonperfused (normal) left kidney was removed at day 14 and the kidney function was measured at day 17, followed by sacrifice and kidney biopsy.

Figure 16A:
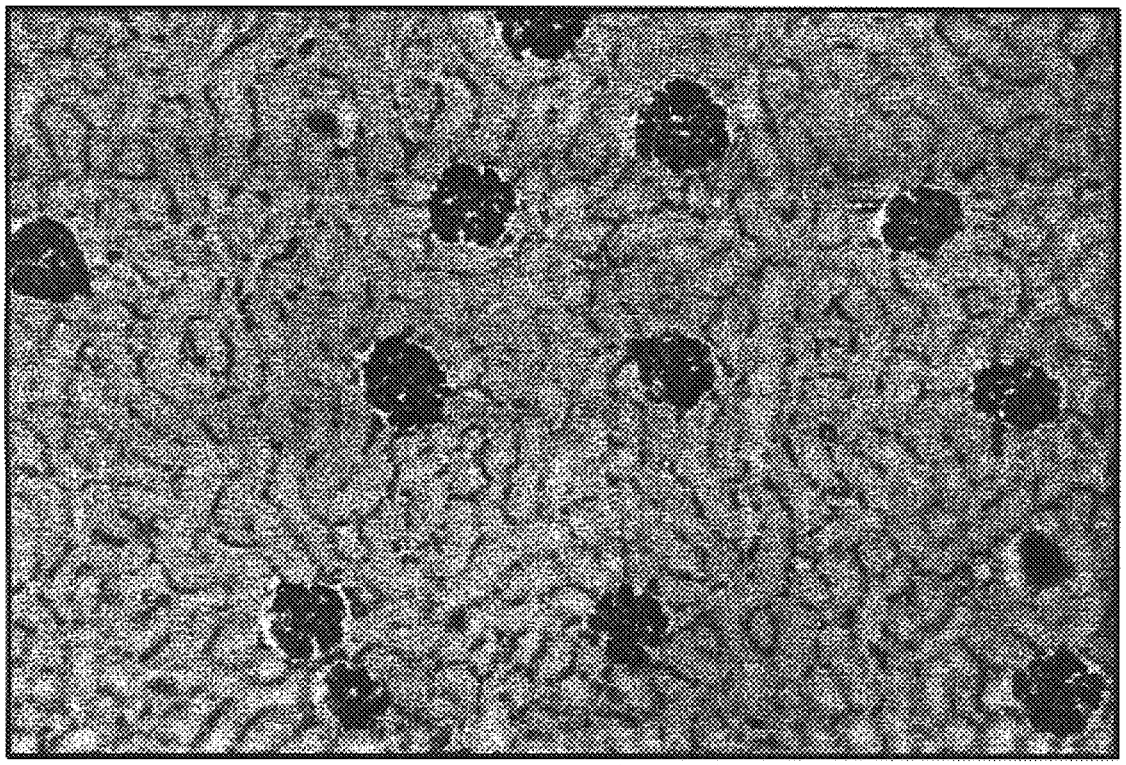
FIGS. 16A–16D shows that VEGF infusion stimulates capillary remodeling and angiogenesis in the HUS model. (A) normal pattern of endothelial staining; (B) endothelial staining 24 hours after injury; (C) recovery of capillary density in vehicle-treated rats; (D) recovery of capillary density in VEGF-treated rats.
Figure 16B:
Figure 16C:
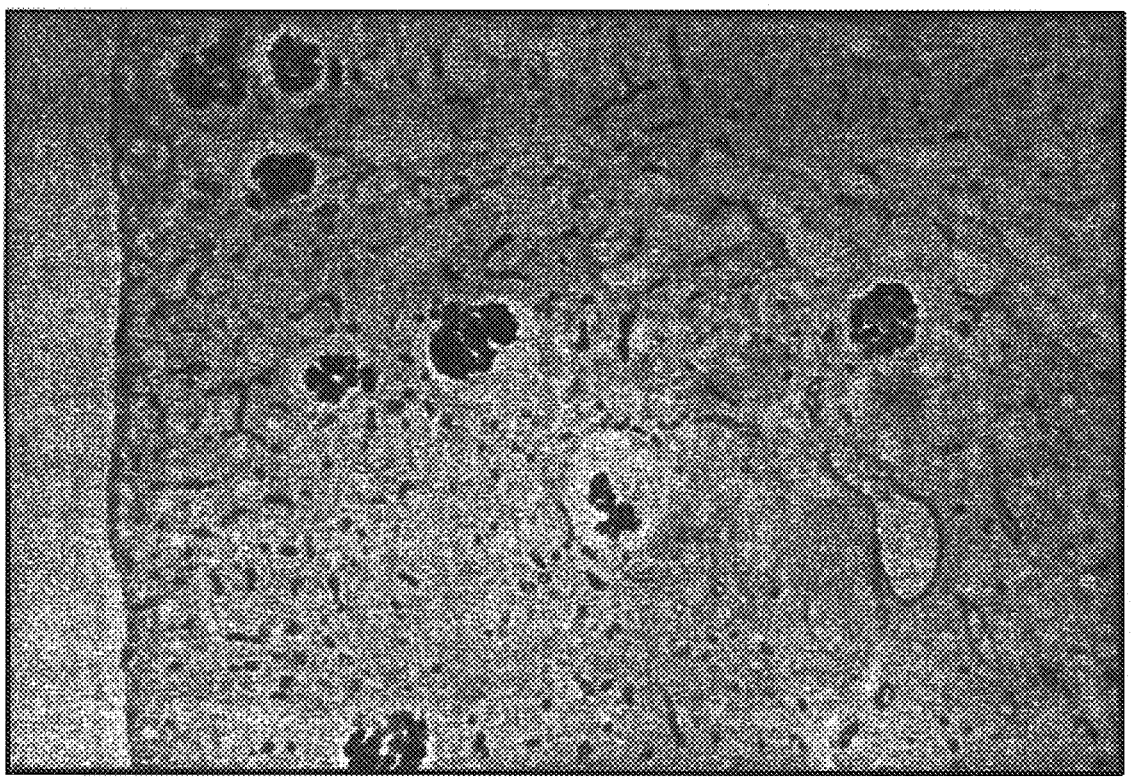
Figure 16D:
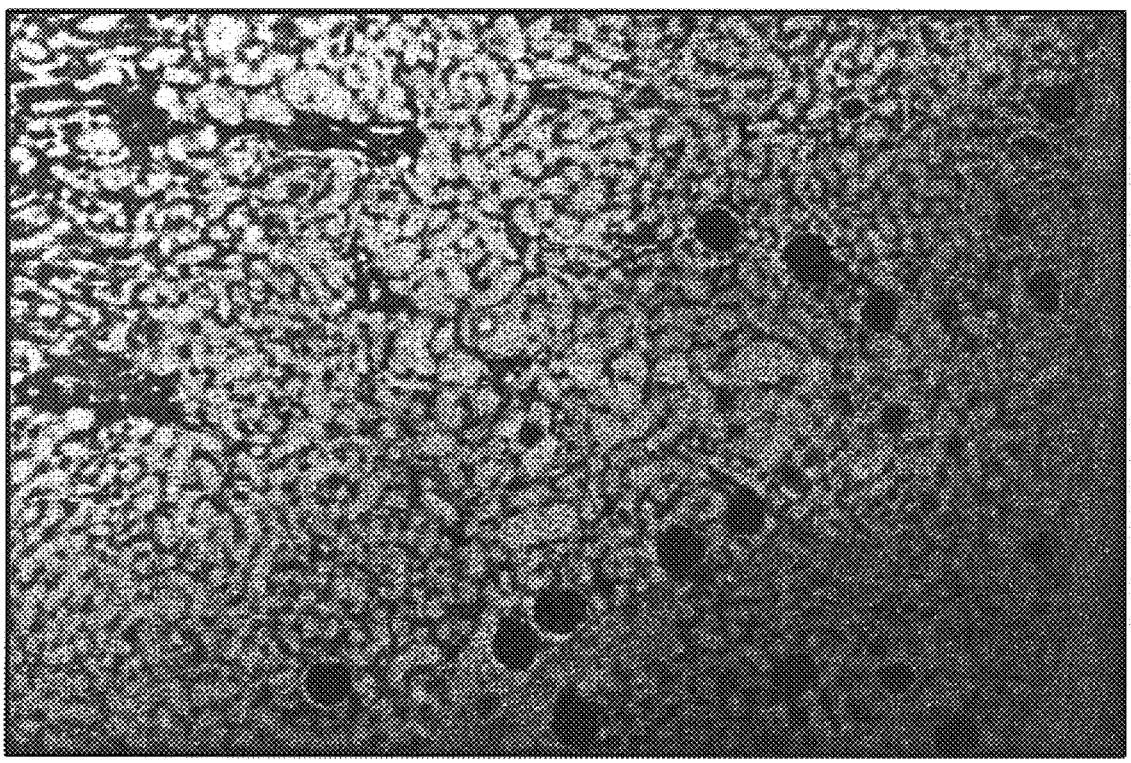

In contrast to the normal pattern of endothelial cell staining (FIG. 16A), at 24 hours after injury, both GEN and PEN injury were widespread, with large areas showing the absence of endothelial cells (FIG. 16B). During the subsequent 10 days, significant recovery of capillary density could be documented in vehicle-treated rats (FIG. 16C), but capillary density was significantly greater in VEGF-treated rats (FIG. 16D). This was associated with increased number of intact glomeruli, preservation of the cortical volume, and better renal function (Table 3). Furthermore, although capillary repair occurred in control rats, VEGF-treated rats showed a greater recovery of capillary density, increased urinary nitrites and increased eNOS expression, as determined by immunostaining (Table 3).

TABLE 3

| Parameter | VEGF (n = 6) | Vehicle (n = 6) |
|---|---|---|
| Intact glomeruli (>75% with +GEN stain) (#/mm$^2$) | 2.0 ± 0.1 | 1.6 ± 0.1* |
| Capillary density (%) | 98.1 ± 1.2 | 96.0 ± 1.2* |
| Arteriolar density (#/mm$^2$) | 4.58 ± 0.23 | 3.25 ± 0.4* |
| Capillary rarefaction (%) | 1.9 ± 1.2 | 4.0 ± 1.3* |
| Interstitial fibrosis (%) | 10.2 ± 3.7 | 25.7 ± 4.6* |
| Cortical thickness (mm) | 1.32 ± 0.05 | 1.11 ± 0.02* |
| BUN (mg/dl) | 68 ± 8 | 172 ± 40* |
| Urinary nitrites (nmol/d) | 1913 ± 180 | 786 ± 400* |

* p < 0.05

All analyses were performed using midcoronal sections. Capillary density was measured as the % of 0.1 mm$^2$ areas with capillaries noted by computer image analysis sing an endothelial cell specific antibody. Arteriolar density was measured by counting the number of α-actin positive arterioles per mm$^2$. Capillary rarefaction index is the % of 0.1 mm$^2$ tissue that lacks capillaries. Interstitial fibrosis was measured by computer image analysis.

Control rats developed microvascular injury, glomerular injury and tubulointerstitial (TI) fibrosis and renal failure. VEGF treatment initiated 24 hours after injury was associated with increased renal arteriolar and interlobular artery density (4.58±0.23 vs. 3.25±0.38/mm$^2$, p=0.01) in association with less glomerular ischemia (0.04±0.01 vs. 0.14±0.04 collapsed glomeruli/mm$^2$, p=0.03). VEGF treatment was also associated with decreased TI fibrosis (10.2±3.7 vs. 25.7±4.6%, p=0.03), increased cortical thickness (1.32±0.05 vs. 1.11±0.02 mm, p<0.01), and improved renal function (BUN 68±8 vs. 172±40 mg/dl, p+0.03). VEGF treatment was associated with an increased urinary nitrates/nitrites (NOx) concentration (1913±180 vs. 786±400 nmol/day, p=0.02). In contrast to the effect of VEGF when it is administered one hour after the antibody infusion (Example 1), we noted no effect of VEGF on renal infarction (3.7±1.7 vs. 1.9±2.2%, p=NS). The dose of antibody was chosen to minimize infarction.

We conclude that VEGF treatment initiated after acute TMA is established improves renal function and histology.

In classical epidemic HUS, it is well accepted that verotoxin-induced GEN injury mediates the disease. In the present, HUS-like models, endothelial cell injury has been induced by selective perfusion of the renal artery with anti-GEN antibody. In an ideal animal model of HUS, GEN injury would be induced by verotoxins. However, endothelial cells are no susceptible to verotoxins in most experimental animals and there are potential non-infective causes of HUS in which GEN injury plays pivotal roles in the pathogenesis of the diseases (Remuzzi and Ruggenenti, *Kidney Int.* 48:2–19 (1995)). Therefore, the model described in the foregoing examples is believed to be of great significance to examine the pathophysiology and treated of HUS. Positive results in this model are indicative of potential human clinical utility.

These studies provide strong and suggestive evidence that VEGF infusion may have the ability to reduce cortical necrosis in experimental TMA. Given the observation that cortical necrosis is one of the major risk factors predicting a poor long term outcome on renal function (Habib et al., *Adv. Nephrology* 11:99–128 (1982)), these studies suggest that VEGF may also have a beneficial effect on both acute and chronic renal function in HUS and related thrombotic microangiopathies. It has been reported recently that GEN injury takes place in several forms and that persistent GEN injury may be relevant to the development of glomerular sclerosis (Iruela et al., *Am. J. Pathol.* 147:1715–1727 (1995); Kitamura et al., *Exp. Nephrol.* 6:328–336 (1998)). Prevention of endothelial cell injury by VEGF may provide a new strategy for the treatment of chronic renal disease in the future.

What is claimed is:

1. A method for inhibiting the development of injury to blood vessels associated with microvascular angiopathy, or repairing such injury, comprising providing an effective amount of a vascular endothelial growth factor (VEGF), wherein said VEGF promotes vascular endothelial cell growth.

2. The method of claim 1 wherein said blood vessels are in non-tumor tissues of adults or children.

3. The method of claim 1 wherein said microvascular angiopathy is a thrombolytic microangiopathy (TMA).

4. The method of claim 1 wherein said VEGF is a human VEGF.

5. The method of claim 4 wherein said VEGF is hVEGF$_{121}$ or hVEGF$_{165}$.

6. The method of claim 5 wherein said VEGF is in dimeric form.

7. The method of claim 6 wherein at least one monomer within said dimer is unglycosylated.

8. The method of claim 7 wherein each monomer within said dimer is unglycosylated.

9. The method of claim 6 wherein said dimer is a heterodimer.

10. The method of claim 1 wherein said VEGF exerts its activity primarily via effects other than inducing new blood vessel formation.

11. The method of claim 3 wherein said TMA is in the kidney.

12. The method of claim 13 wherein said TMA is associated with a chronic renal disease.

13. The method of claim 13 wherein said TMA is associated with an acute renal disease.

14. The method of claim 10 for the prevention or treatment of TMA associated with hemolytic uremic syndrome (HUS).

15. The method of claim 14 wherein said HUS is thrombotic thrombocytopenic purpura (TTP).

16. The method of claim 3 wherein said TMA is in the heart.

17. The method of claim 3 wherein said MTA is in the lungs.

18. A method for inhibiting the development of injury to nonvascular tissue associated with microvascular angiopathy, or repairing such injury, comprising providing an effective amount of a vascular endothelial growth factor (VEGF), wherein said VEGF promotes vascular endothelial cell growth.

19. The method of claim 18 wherein said treatment maintains the normal function of an organ comprising said nonvascular tissue.

20. The method of claim 19 wherein said organ is the kidney.

21. The method of claim 20 which improves renal function after acute TMA.

22. The method of claim 19 wherein said organ is the heart.

23. The method of claim 19 wherein said organ is the lungs.

24. The method of claim 18 wherein said VEGF is a human VEGF.

25. The method of claim 24 wherein said human VEGF is hVEGF$_{121}$ or hVEGF$_{165}$.

26. A method for inhibiting the development of hemolytic uremic syndrome (HUS), or treating HUS, comprising providing to a patient at risk of developing or having diagnosed with HUS an effective amount of a vascular endothelial growth factor (VEGF), wherein said VEGF promotes vascular endothelial cell growth.

27. The method of claim 26 wherein said VEGF is a human vascular endothelial growth factor (VEGF).

28. The method of claim 27 wherein said human VEGF is hVEGF$_{121}$ or hVEGF$_{165}$.

* * * * *

UNITED STATES PATENT AND TRADEMARK OFFICE
CERTIFICATE OF CORRECTION

PATENT NO. : 6,677,300 B1 Page 1 of 1
APPLICATION NO. : 09/392931
DATED : January 13, 2004
INVENTOR(S) : George F. Schreiner et al.

It is certified that error appears in the above-identified patent and that said Letters Patent is hereby corrected as shown below:

On the title page item (73),
The Assignees should be:

Scios, Inc., Sunnyvale, CA (US)

and

The University of Washington, Seattle, WA (US)

Signed and Sealed this

Third Day of October, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,677,300 B1 | Page 1 of 1 |
| APPLICATION NO. | : 09/392931 | |
| DATED | : January 13, 2004 | |
| INVENTOR(S) | : George F. Schreiner et al. | |

It is certified that error appears in the above-identified patent and that said Letters Patent is hereby corrected as shown below:

Col. 1, line 6, following the paragraph entitled "Cross-reference to Related Applications," the following paragraph should be inserted:

--Government Funding

This invention was made with US Government support under grant number NIDDK DK52121 awarded by the National Institutes of Health. The US Government has certain rights in this invention.--

Signed and Sealed this

Seventeenth Day of April, 2007

JON W. DUDAS
*Director of the United States Patent and Trademark Office*

SEQUENCE LISTING

<160> NUMBER OF SEQ ID NOS: 11

<210> SEQ ID NO 1
<211> LENGTH: 444
<212> TYPE: DNA
<213> ORGANISM: Homo sapien

<400> SEQUENCE: 1

```
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240 atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga aagatagagc aagacaagaa     420
aaatgtgaca agccgaggcg gtga                                            444
```

<210> SEQ ID NO 2
<211> LENGTH: 147
<212> TYPE: PRT
<213> ORGANISM: Homo sapien

<400> SEQUENCE: 2

```
Met Asn Phe Leu Leu Ser Trp Val His Trp Ser Leu Ala Leu Leu Leu
 1               5                  10                  15
Tyr Leu His His Ala Lys Trp Ser Gln Ala Ala Pro Met Ala Glu Gly
             20                  25                  30
Gly Gly Gln Asn His His Glu Val Val Lys Phe Met Asp Val Tyr Gln
         35                  40                  45
Arg Ser Tyr Cys His Pro Ile Glu Thr Leu Val Asp Ile Phe Gln Glu
     50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                 85                  90                  95
Thr Glu Glu Ser Asn Ile Thr Met Gln Ile Met Arg Ile Lys Pro His
             100                 105                 110
Gln Gly Gln His Ile Gly Glu Met Ser Phe Leu Gln His Asn Lys Cys
         115                 120                 125
Glu Cys Arg Pro Lys Lys Asp Arg Ala Arg Gln Glu Lys Cys Asp Lys
    130                 135                 140
Pro Arg Arg
145
```

<210> SEQ ID NO 3
<211> LENGTH: 516
<212> TYPE: DNA
<213> ORGANISM: Homo sapien

<400> SEQUENCE: 3

```
atgaactttc tgctgtcttg ggtggattgg agccttgcct tgctgctcta cctccaccat      60
gccaagtggt cccaggctgc acccatggca gaaggaggag gcagaatca tcacgaagtg     120
gtgaagttca tggatgtcta tcagcgcagc tactgccatc caatcgagac cctggtggac     180
atcttccagg agtaccctga tgagatcgag tacatcttca gccatcctg tgtgccctg      240
atgcgatgcg ggggctgctg caatgacgag ggcctggagt gtgtgcccac tgaggagtcc     300
aacatcacca tgcagattat gcggatcaaa cctcaccaag ccagcacat aggagagatg     360
agcttcctac agcacaacaa atgtgaatgc agaccaaaga agatagagc aagacaagaa     420
aaaaaatcag ttcgaggaaa gggaaagggg caaaaacgaa agcgcaagaa atcccggtat     480
aagtcctgga gcgtatgtga caagccgagg cggtga                              516
```

<210> SEQ ID NO 4
<211> LENGTH: 145
<212> TYPE: PRT
<213> ORGANISM: Homo sapien

<400> SEQUENCE: 4

```
Ala Pro Met Ala Glu Gly Gly Gly Gln Asn His His Glu Val Val Lys
 1               5                  10                  15
Phe Met Asp Val Tyr Gln Arg Ser Tyr Cys His Pro Ile Glu Thr Leu
             20                  25                  30
Val Asp Ile Phe Gln Glu Tyr Pro Asp Glu Ile Glu Tyr Ile Phe Lys
         35                  40                  45
Pro Ser Cys Val Pro Leu Met Arg Cys Gly Gly Cys Cys Asn Asp Glu
     50                  55                  60
```

Gly Leu Glu Cys Val Pro Thr Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Lys Lys Ser Val Arg Gly Lys Gly Lys Gly Lys Arg Lys
                115                 120                 125

Arg Lys Lys Ser Arg Tyr Lys Ser Trp Ser Val Cys Asp Lys Pro Arg
    130                 135                 140

Arg
145

<210> SEQ ID NO 5
<211> LENGTH: 576
<212> TYPE: DNA
<213> ORGANISM: Homo sapien

<400> SEQUENCE: 5
atgaactttc tgctgtcttg ggtgcattgg agcctcgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgccctg      240 atgcgatgcg ggggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga agatagagc aagacaagaa      420 aatccctgtg ggccttgctc agagcggaga aagcatttgt ttgtacaaga tccgcagacg     480
tgtaaatgtt cctgcaaaaa cacagactcg cgttgcaagg cgaggcagct tgagttaaac     540
gaacgtactt gcagatgtga caagccgagg cggtga                             576

<210> SEQ ID NO 6
<211> LENGTH: 191
<212> TYPE: PRT
<213> ORGANISM: Homo sapien

<400> SEQUENCE: 6

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
                115                 120                 125

Glu Cys Arg Pro Lys Lys Asp Arg Ala Arg Gln Glu Asn Pro Cys Gly

```
                130               135               140
Pro Cys Ser Glu Arg Arg Lys His Leu Phe Val Gln Asp Pro Gln Thr
145               150               155               160

Cys Lys Cys Ser Cys Lys Asn Thr Asp Ser Arg Cys Lys Ala Arg Gln
                165               170               175

Leu Glu Leu Asn Glu Arg Thr Cys Arg Cys Asp Lys Pro Arg Arg
                180               185               190

<210> SEQ ID NO 7
<211> LENGTH: 642
<212> TYPE: DNA
<213> ORGANISM: Homo sapien

<400> SEQUENCE: 7
atgaactttc tgctgtcttg ggtgcattgg agcctcgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgcccctg     240
atgcgatgcg ggggctgctg caatgacgag ggcctggagt gtgtgcccac tgaggagtcc     300
aacatcacca tgcagattat gcggatcaaa cctcaccaag ccagcacat aggagagatg      360 agcttcctac agcacaacaa atgtgaatgc agaccaaaga agatagagc aagacaagaa      420 aaaaaatcag ttcgaggaaa gggaaagggg caaaaacgaa agcgcaagaa atcccggtat     480
aagtcctgga gcgtggggcc ttgctcagag cggagaaagc atttgtttgt acaagatccg     540
cagacgtgta atgttcctg caaaaacaca gactcgcgtt gcaaggcgag gcagcttgag      600
ttaaacgaac gtacttgcag atgtgacaag ccgaggcggt ga                        642

<210> SEQ ID NO 8
<211> LENGTH: 215
<212> TYPE: PRT
<213> ORGANISM: Homo sapien

<400> SEQUENCE: 8

Met Asn Phe Leu Leu Ser Trp Val His Trp Ser Leu Ala Leu Leu Leu
1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
        130                 135                 140

Arg Gly Lys Gly Lys Gly Gln Lys Arg Lys Arg Lys Lys Ser Arg Tyr
145                 150                 155                 160
```

```
Lys Ser Trp Ser Val Pro Cys Gly Pro Cys Ser Glu Arg Arg Lys His
                165                 170                 175
Leu Phe Val Gln Asp Pro Gln Thr Cys Lys Cys Ser Cys Lys Asn Thr
                180                 185                 190
Asp Ser Arg Cys Lys Ala Arg Gln Leu Glu Leu Asn Glu Arg Thr Cys
                195                 200                 205
Arg Cys Asp Lys Pro Arg Arg
        210             215
```

<210> SEQ ID NO 9
<211> LENGTH: 699
<212> TYPE: DNA
<213> ORGANISM: Homo sapien

<400> SEQUENCE: 9

```
atgaactttc tgctgtcttg ggtgcattgg agcctcgcct tgctgctcta cctccaccat    60
gccaagtggt cccaggctgc acccatggca gaaggaggag ggcagaatca tcacgaagtg   120
gtgaagttca tggatgtcta tcagcgcagc tactgccatc caatcgagac cctggtggac   180
atcttccagg agtaccctga tgagatcgag tacatcttca agccatcctg tgtgcccctg   240
atgcgatgcg ggggctgctg caatgacgag ggcctggagt gtgtgcccac tgaggagtcc   300
aacatcacca tgcagattat gcggatcaaa cctcaccaag ccagcacat aggagagatg    360
agcttcctac agcacaacaa atgtgaatgc agaccaaaga agatagagc aagacaagaa    420
aaaaaatcag ttcgaggaaa gggaaagggg caaaaacgaa agcgcaagaa atcccggtat   480
aagtcctgga gcgtgtacgt tggtgcccgc tgctgtctaa tgccctggag cctccctggc   540
ccccatccct gtgggccttg ctcagagcgg agaaagcatt tgtttgtaca agatccgcag   600
acgtgtaaat gttcctgcaa aaacacagac tcgcgttgca aggcgaggca gcttgagtta   660
aacgaacgta cttgcagatg tgacaagccg aggcggtga                         699
```

<210> SEQ ID NO 10
<211> LENGTH: 110
<212> TYPE: PRT
<213> ORGANISM: Homo sapien

<400> SEQUENCE: 10

```
Ala Pro Met Ala Glu Gly Gly Gln Asn His His Glu Val Val Lys
 1               5                  10                  15
Phe Met Asp Val Tyr Gln Arg Ser Tyr Cys His Pro Ile Glu Thr Leu
                20                  25                  30
Val Asp Ile Phe Gln Glu Tyr Pro Asp Glu Ile Glu Tyr Ile Phe Lys
            35                  40                  45
Pro Ser Cys Val Pro Leu Met Arg Cys Gly Gly Cys Cys Asn Asp Glu
        50                  55                  60
Gly Leu Glu Cys Val Pro Thr Glu Glu Ser Asn Ile Thr Met Gln Ile
65                  70                  75                  80
Met Arg Ile Lys Pro His Gln Gly Gln His Ile Gly Glu Met Ser Phe
                85                  90                  95
Leu Gln His Asn Lys Cys Glu Cys Arg Pro Lys Lys Asp Arg
                100                 105                 110
```

<210> SEQ ID NO 11
<211> LENGTH: 110
<212> TYPE: PRT
<213> ORGANISM: Homo sapien -continued

```
<400> SEQUENCE: 11

Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
                100                 105                 110
```